United States Patent
Eggink et al.

(10) Patent No.: US 10,624,965 B2
(45) Date of Patent: Apr. 21, 2020

(54) IMMUNOTHERAPY TREATMENTS AND COMPOSITIONS

(71) Applicant: SUSAVION BIOSCIENCES, INC., Tempe, AZ (US)

(72) Inventors: Laura L. Eggink, Scottsdale, AZ (US); J. Kenneth Hoober, Phoenix, AZ (US)

(73) Assignee: Susavion Biosciences, Inc., Tempe, AZ (US)

( * ) Notice: Subject to any disclaimer, the term of this patent is extended or adjusted under 35 U.S.C. 154(b) by 239 days.

(21) Appl. No.: 15/537,731

(22) PCT Filed: Dec. 17, 2015

(86) PCT No.: PCT/US2015/066400
§ 371 (c)(1),
(2) Date: Jun. 19, 2017

(87) PCT Pub. No.: WO2016/100679
PCT Pub. Date: Jun. 23, 2016

(65) Prior Publication Data
US 2019/0167789 A1    Jun. 6, 2019

Related U.S. Application Data

(60) Provisional application No. 62/094,944, filed on Dec. 19, 2014.

(51) Int. Cl.
*A61K 38/10* (2006.01)
*A61K 39/395* (2006.01)
*A61K 39/00* (2006.01)

(52) U.S. Cl.
CPC .......... *A61K 39/3955* (2013.01); *A61K 38/10* (2013.01); *A61K 39/0011* (2013.01); *A61K 2039/507* (2013.01); *A61K 2039/585* (2013.01); *A61K 2039/6056* (2013.01); *A61K 2039/64* (2013.01)

(58) Field of Classification Search
CPC ............ A61K 39/3955; A61K 39/0011; A61K 38/10; A61K 2039/6056; A61K 2039/64; A61K 2039/585; A61K 2039/505
See application file for complete search history.

(56) References Cited

U.S. PATENT DOCUMENTS

| | | | |
|---|---|---|---|
| 8,168,757 B2 | 5/2012 | Finnefrock et al. | |
| 2012/0064035 A1* | 3/2012 | Hadden | A61K 38/164 424/85.2 |
| 2013/0004483 A1* | 1/2013 | Totterman | G01N 33/5011 424/133.1 |
| 2013/0309250 A1* | 11/2013 | Cogswell | C07K 16/2827 424/172.1 |
| 2014/0099254 A1 | 4/2014 | Chang et al. | |
| 2014/0105912 A1 | 4/2014 | Noelle | |

FOREIGN PATENT DOCUMENTS

| | | |
|---|---|---|
| WO | 2005087793 A2 | 9/2005 |
| WO | 2008076815 A2 | 6/2008 |
| WO | 2013096829 A2 | 6/2013 |

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Eggink, Laura et al., "A biologically active peptide mimetic of N-acetylgalactosamine/galactose", BMC Research Notes, 2(1):23 (Feb. 11, 2009).
Kyi, Chrisann et al., "Checkpoint blocking antibodies in cancer immunotherapy", FEBS Letters, 588:368-376 (Oct. 23, 2013).
Matsubara, Teruhiko, "Potential of Peptides as Inhibitors and Mimotopes: Selection of Carbohydrate-Mimetic Peptides from Phage Display Libraries", Journal of Nucleic Acids, 2012:1-15 (Jan. 1, 2012).
Lepenies, Bernd et al., "Targeting C-type lectin receptors with multivalent carbohydrate ligands", Advanced Drug Delivery Reviews, 65:1271-1281 (2013).
English translation of Office Action for Japanese Patent Application No. 2017-533220 dated Aug. 13, 2019.

* cited by examiner

*Primary Examiner* — Phuong Huynh
(74) *Attorney, Agent, or Firm* — Rodney J. Fuller; Booth Udall Fuller, PLC

(57) ABSTRACT

The present invention relates to compositions and kits comprising a peptide that activate the immune response and methods of using the composition for immunotherapy and cancer treatments. The peptide comprises an active peptide sequence of VQATQSNQHTPR. In some embodiments, the peptide may be tetravalent. For example, the peptide has the structure [(VQATQSNQHTPRGGGS)$_2$K]$_2$K—NH$_2$. In some embodiments, the compositions and methods are directed to the treatment of cancer and/or infections.

16 Claims, 16 Drawing Sheets
Specification includes a Sequence Listing.

B

IMMUNOTHERAPY TREATMENTS AND COMPOSITIONS

RELATED APPLICATION DATA

This application is the U.S. National Stage of International Application No. PCT/US2015/066400, filed on Dec. 17, 2015, which claims the benefit of and priority to U.S. Provisional Application No. 62/094,944, filed Dec. 19, 2014, the contents of each of which are hereby incorporated by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 1,017 byte ASCII (text) file named "24667_040_Seq_List_v2" created on Oct. 28, 2019.

FIELD OF THE INVENTION

The present invention relates to compositions comprising a peptide that activate the immune response and methods of using the compositions for immunotherapy, including for the treatment of cancer.

BACKGROUND OF THE INVENTION

In vertebrates, the immune system comprises the innate immune system and the adaptive immune system. Whereas the innate immune response recognizes pathogens in a non-specific way, for example through pattern-associated molecular patterns that distinguish pathogens from host molecules, the adaptive immune system is directed to specific antigens. Specificity of the adaptive immune response is taught by interaction with antigens, which are presented as a complex with major histocompatibility molecules (MHC) to adaptive immune cells. Several T cell subgroups can be activated by antigen presentation.

Interaction of the naïve T cell with the MHC complex requires interaction with CD4 or CD8 in addition to binding of the antigen by the T cell receptor (TCR). Class I MHC can be expressed on nearly every nucleated cell of the body, and it interacts with CD8, which is predominantly expressed on the cytotoxic class of T cells. These cells can induce the death of the cells presenting the antigen that resulted in the activation of the cell, so they are heavily regulated to prevent tissue damage. Activation of cytotoxic T cells requires strong MHC complex signal or additional activation provided by helper T cells. Helper T cells are characterized by CD4 expression, so they interact with the class II MHC. While these cells have no ability to kill cells carrying the antigen that resulted in its activation, these cells manage the immune response mounted by the antigen. Activation of naïve helper T cells results in the release of cytokines that can activate antigen-presenting cells or activate cytotoxic T cells. For example, Th1 or Th2 helper T cells enhance immune responses to different types of antigens. A Th1 response, which is characterized by the release of interferon-γ (IFNγ), leads to the activation of phagocytes, cytotoxic T cells, and the release of various cytokines in response to an antigen. A Th2 response, which is characterized by the release of interleukin-4 (IL-4), leads to the responses mediated by macromolecules found in extracellular fluids such as secreted antibodies, complement proteins and certain antimicrobial peptides.

The immune system also provides for immune suppression to limit the damaging potential of an immune response. The immunosuppressive regulatory T cell sub-population of T cells attenuates a cytotoxic T cell response, and normally protects against over-stimulation and development of auto-immunity. Even prior to differentiation into naïve T cells, a group of T cell precursors differentiate into natural regulatory T cells in the thymus by moderate interaction with the self-peptide MHC complex. Regulatory T cells also include inducible regulatory T cells developed from $CD4^+$ T cells outside of the thymus. Whereas natural regulatory T cells suppress T cell activation by interaction with antigen-presenting cells to produce negative signals for T cell activation, inducible regulatory T cells produce cytokines that inhibit T cell proliferation.

Imbalance between the active and suppressive immune response can result in diseases and conditions such as cancer, immunodeficiency (e.g., acquired immunodeficiency syndrome), autoimmune diseases, or hypersensitivity reactions or worsen diseases and infections, for example, tuberculosis, *Leishmania*, or malaria.

As immune cells patrol the body for potential dangers, immune cells also eliminate tumors. A strong, anti-cancer immune response requires antibodies (the adaptive, humoral arm) and an active cell-mediated arm. The interplay between these two arms is driven by activation of dendritic cells (the primary antigen-presenting cell type, APCs) and subsequent production of antibodies by B cells. Destruction of cancer cells then occurs by two processes: a cytotoxic cellular response by neutrophils, natural killer cells, cytotoxic T cells, and macrophages, and an antibody-dependent cellular cytotoxicity (ADCC) performed by activated macrophages and neutrophils. Often tumor cells can be made more susceptible to digestion for antigen presentation by radiation treatment or chemotherapy. Activation of these cells provides a multi-pronged approach that should overcome immune suppression or "evasion of immune destruction," a major hallmark of cancer [Hanahan and Weinberg, 2011]. Whereas Hanahan and Weinberg support the 'somatic mutation theory' for the origin of cancer, Sonnenschein et al. (2014) provided an alternate proposal that cancer results from a breakdown of tissue organization, or the 'tissue organization field theory."

A goal of immunotherapy is to restore the ability of the immune system to overcome these diseases. Traditional immunotherapy targets have been antigens specific to the targeted cells, such as tumor-associated antigens (e.g., $T_n$ antigen or $T_f$ antigen) or glycosylation groups expressed on the surface of viruses or bacteria or on cells infected by the viruses or bacteria. For example, vaccinations using these antigens induce endogenous production of antibodies against these antigens to mount an immune response. The traditional approach also uses adjuvants to aid the stimulation of the immune system, but greater understanding of immune responses have expanded the potential candidates for factors that activate immune cells to stimulate the immune system either directly or indirectly to mount an immune response. Understanding of immune checkpoints has enabled immunotherapy to target proteins involved in regulating the balance of the immune response, for example, to suppress or enhance the population of regulatory T cells. Thus immunotherapy is now able to 1) induce endogenous production of antibodies, 2) provide exogenous antibodies that manipulate the type of immune response to be mounted, and 3) activate or suppress specific immune cells by factors from the immune system checkpoint.

The present invention is directed to combinations of these approaches for improved immunotherapy, for example, to boost the immunogenicity of tumors. In particular, the present invention is directed to the use of peptides in combination with antibodies, such as exogenous antibodies against immune checkpoint proteins or against cancer markers. Peptides that mimic sugars and bind to regulatory lectin-type receptors expressed by key cells of the immune system can enhance the immune responses, which can support the therapeutic benefits of the exogenous antibodies.

SUMMARY OF THE INVENTION

The present invention provides compositions and kits that activate the adaptive immune response comprising a therapeutically effective amount of a peptide that has an active peptide sequence represented by SEQ ID NO:1 (VQATQS-NQHTPR; also referred to herein as "svL4") and a therapeutically effective amount of a first antibody. The peptide may be tetravalent. For example, the peptide has the structure [(VQATQSNQHTPRGGGS)$_2$K]$_2$K—NH$_2$ (SEQ ID NO:3). In some embodiments, the first antibody is against an immune checkpoint protein. In some aspects, the compositions and kits may comprise a second antibody, wherein the second antibody is against an immune checkpoint protein of a different immune checkpoint pathway as the first antibody. Embodiments of the invention may further comprise a pharmaceutically acceptable carrier. The immune checkpoint proteins are selected from at least one of cytotoxic T lymphocyte antigen 4 (CTLA-4), programmed death 1 (PD-1), or ligands to PD-1, such as programmed death-ligand 1 (PD-L1) and programmed death-ligand 2 (PD-L2) in some embodiments.

The therapeutically effective amount is an amount sufficient to activate the immune response in a subject. In some aspects, the therapeutically effective amount is an amount sufficient to treat cancer in a subject. The cancer may be bladder cancer, brain cancer, breast cancer, colon cancer, head and neck cancer, liver cancer, lung cancer, pancreatic cancer, prostrate cancer, ovarian cancer, kidney cancer, or skin cancer, for example, colorectal adenocarcinoma, glioblastoma, hepatocellular carcinoma, hormone-refractory prostate cancer, epithelial ovarian carcinoma, ovarian adenocarcinoma, melanoma, mesothelioma, non-small cell lung cancer, small cell lung cancer, or renal cell carcinoma.

In some embodiments, the therapeutically effective amount is an amount sufficient to suppress the population of regulatory T cells. In another embodiment, the therapeutically effective amount is an amount sufficient to increase the population of effector T cells. In still another embodiment, the therapeutically effective amount is an amount sufficient to increase the levels of anti-cancer cytokines such as IL-2, IL-12p70, IL-21, IL-27, TNFα, and IFNγ. In some aspects, the level of anti-cancer cytokines increases by several folds. In some embodiments, the therapeutic amount of the first peptide and the second peptide is between about 0.1 nmol/kg body weight to about 1500 nmol/kg body weight, between about 1 nmol/kg body weight to about 1 1000 nmol/kg body weight, or about 1 nmol/kg body weight.

The present invention further provides methods of activating the adaptive immune response in a subject by administering a therapeutically effective amount of a peptide to a subject, wherein the peptide has an active peptide sequence represented by SEQ ID NO:1; and administering a therapeutically effective amount of an antibody, wherein the antibody is against an immune checkpoint protein. In some aspects, the antibody comprises antibodies against immune checkpoint proteins of two distinct immune checkpoint pathways. In some embodiments, the peptide administered is tetravalent. In these embodiment, active peptide sequence is connected to the core by a linker sequence. In preferred embodiments, the core is a tri-lysine core, and the linker sequence is -GGGS- (SEQ ID NO:2). For example, a tetravalent peptide has the structure [(VQATQSNQHT-PRGGGS)$_2$K]$_2$K—NH$_2$ (SEQ ID NO:3).

In one implementation, the method comprises administering the peptide before administering the antibody, for example, at least three days before the administration of the antibody. After which, the peptide is administered concurrently with the administration of the antibody. In other implementations, the peptide and the antibody are administered together at the start of the treatment. In some implementations, the peptide is administered on alternating days or on a weekly basis. In some embodiments, administration of the peptide is continued after the period of antibody treatment.

DETAILED DESCRIPTION OF THE INVENTION

Figure 1:
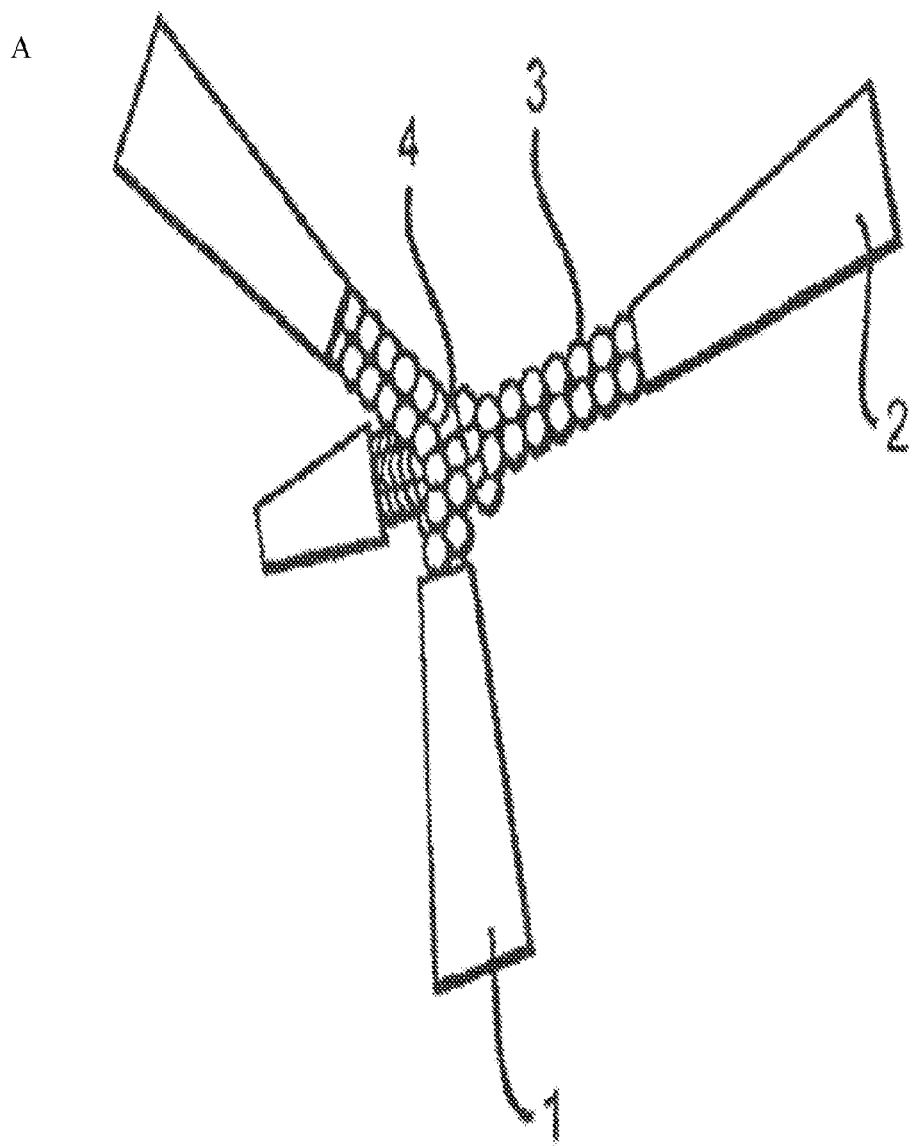
FIG. 1 depicts the structure of tetravalent svL4, with the active sequence presented as SEQ ID NO:1 (VQATQSN-QHTPR). A: Schematic design of peptide. Arms with active sequences (1, 2) are connected via a spacer sequence (3) to a tri-lysine core (4). B: Chemical structure of the peptide with a C-terminal amide. The peptides are composed entirely of naturally occurring L-amino acids, where A is alanine, G is glycine, H is histidine, K is lysine, L is leucine, N is asparagine, P is proline, Q is glutamine, R is arginine, S is serine, T is threonine, and V is valine. The sequence -GGGS- (SEQ ID NO:2) is a linker between the active 12-mer sequence and the tri-lysine core. Accordingly, the depicted tetravalent svL4 has the structure [(VQATQSN-QHTPRGGGS)$_2$K]$_2$K—NH$_2$ (SEQ ID NO:3).
Figure 1:
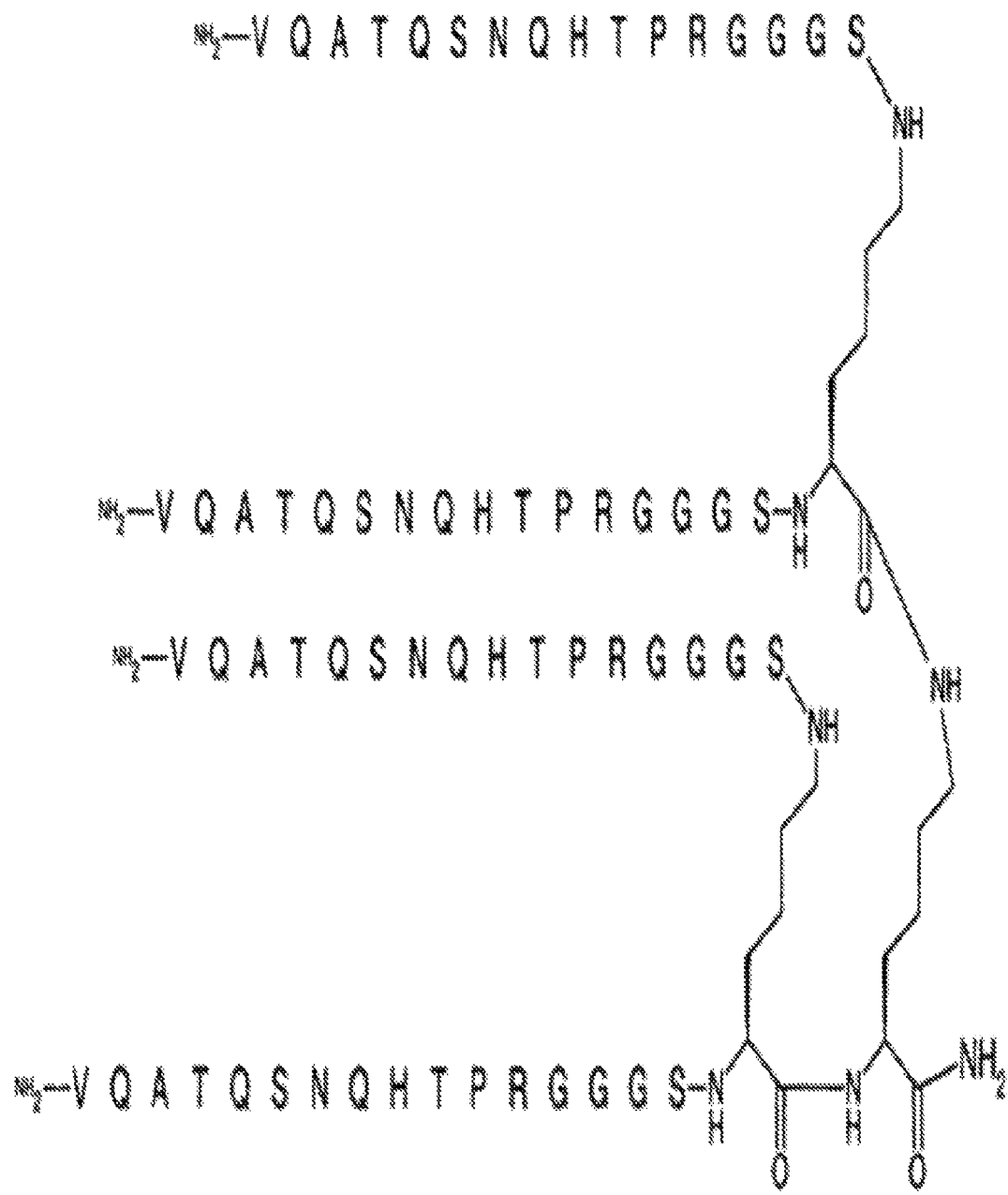

The verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

The term "innate immune response" or "innate immunity" as used herein refers to the response of immune cells to an acute threat from a pathogen. The responses are often inherent reactions to pathogen recognition factors.

The term "adaptive immune response" or "adaptive immunity" as used herein refers to the response of antigen-specific lymphocytes (e.g., T cells and B cells) to antigen, including the development of immunological memory. Adaptive immune responses are generated by clonal selection of lymphocytes.

The term "effector T cell" as used herein refers to T cells that can mediate the removal of pathogens or cells without the need for further differentiation. Thus effector T cells are distinct from naïve T cells and memory T cells, which must differentiate and often proliferate before they become effector cells.

The term "regulatory T cell" or "Treg cell" as used herein refers to T cells that inhibit T-cell responses, particularly by the suppression or down-regulation of effector T cell induction or proliferation. Thus these cells can induce immunological tolerance. Expression of at least one of CD25, CD39, CD73, and Foxp3 is indicative of regulatory T cells. While the majority of regulatory T cells are CD4$^+$, they may also be CD8$^+$. Another indication of regulatory T cells is high expression of cytotoxic T-lymphocyte associated molecule-4 (CTLA-4) or glucocorticoid-induced TNF receptor (GITR).

The term "immune checkpoint" as used herein refers to an inhibitory pathway in the immune system that is crucial for maintaining self-tolerance and modulating the duration and amplitude of physiological immune responses in peripheral tissues in order to minimize collateral tissue damage.

The term "immunotherapy" as used herein refers the treatment of a disease or condition by inducing, enhancing, or suppressing an immune response.

The term "pathogen" as used herein refers to anything that can produce disease. Thus the term includes infectious agents, such as viruses, bacteria, prions, fungi, or protozoans, along with host cells transformed to neoplastic cells.

The present invention relates to a combination immunotherapy approach to activate or enhance the immune response. An optimal adaptive immune response includes the presence of antibodies to mark pathogens and activated cellular components, including macrophages, cytotoxic T cells, natural killer cells and dendritic cells. The invention may inhibit the immunosuppressive responses, enhance the effector T cell responses, or both. In some aspects, the invention enhances the efficacy of effector T cell function, for example by increasing the ratio of effector T cells to regulatory T cells within the tumor and the tumor microenvironment. Preferably, the invention suppresses the population of regulatory T cells within the tumor and the tumor microenvironment. In some aspects, the invention alters the cytokine profile of the subject to enhance to efficacy of effector T cell function, for example, by inducing a several-fold increase of IL-2, IL-12p70, IL-21, IL-27, TNFα, and IFNγ in the serum. In preferred embodiments, the increase in serum levels of these cytokines occurs within around 4 hours of administration of the combination therapy.

The invention treats diseases and conditions in a subject where the immune response mounted by the subject's immune system without outside aid is not able to defend the subject against the disease or condition. Such diseases and conditions may be cancers and persistent infections. Non-limiting examples of cancers that may be treated by the invention are bladder cancer, brain cancer, breast cancer, colon cancer, head and neck cancer, liver cancer, lung cancer, pancreatic cancer, prostate cancer, ovarian cancer, kidney cancer, or skin cancer. In some aspects, the cancers are colorectal adenocarcinoma, glioblastoma, hepatocellular carcinoma, hormone-refractory prostate cancer, ovarian adenocarcinoma, epithelial ovarian carcinoma, melanoma, mesothelioma, non-small cell lung cancer, small cell lung cancer, or renal cell carcinoma. Non-limiting examples of persistent infections include viral infections, mycobacterial infections, and parasitic infections. In some aspects, the viral infection is caused by retroviruses, such as HIV. In some aspects, the mycobacterial infection may be tuberculosis. In some aspects, parasitic infection may be *Leishmania* or malaria.

Peptides of the Combination Therapy

An "off-the-shelf," non-toxic, backbone regime upon which the desired immune response induced by immunotherapy agents (for example, antibodies) may be enhanced makes immunotherapies more effective and less toxic. It is important for the action of immunotherapy agent that the immune system is 'primed' to maximally respond to their presence. In the combination therapy of the present invention, the backbone regime is a foundational peptide regime comprising a peptide that is a mimetic of sugar ligands, for example, the terminal sugars of complex glycans. Peptides are uniquely suited to immunotherapy. Peptides are flexible in design, easily synthesized on a large scale, water soluble and relatively stable, and bind selectively to receptors with high avidity. Their use in immunotherapy is based on their ability to mimic sugars and thus bind to regulatory lectin-type receptors, for example C-type lectin cell-surface receptors, expressed by cells of the immune system [Geijtenbeek and Gringhuis, 2009; Garcia-Vallejo and van Kooyk, 2009]. The peptides bind with much higher avidity than glycan ligands and are suitable for development as drugs. Importantly, a significant level of toxicity does not accompany this approach to immunotherapy.

Preferably, the peptides of the invention bind to regulatory lectin-type receptors of particular benefit for the amplification of the immune response. In one embodiment, the peptide mimics N-acetylgalactosamine (GalNAc), which is found on CD45, for example, the peptide is svL4 (VQATQSNQHTPR; SEQ ID NO:1) (see Examples 1-7). The phosphatase activity of CD45, a widely expressed and abundant cell surface protein, is required for lymphocyte activation and development [Trowbridge and Thomas, 1994]. CD45 removes an inhibitory phosphate from Src family signal transduction kinases [Roskoski, 2005; McNeil et al., 2007], which in T cell activation is expressed as increased TNFα secretion [van Vliet et al., 2006]. Human antigen-presenting cells such as macrophages and immature DCs express the receptor CLEC10a (CD301), which is specific for GalNAc [van Vliet et al., 2008]. Targeting CLEC10a, a strategic target for activation of immune cells, promotes internalization of antigens by DCs, presentation of antigens to CD4 T cells and differentiation of IFNγ-producing CD4$^+$ T cells [Streng-Ouwehand et al. 2011]. Ligand binding to CLEC10a results in enhanced antigen-specific, IFNγ-producing CD8$^+$ T cell responses and tilts naïve CD4$^+$ T cells towards Th1 cells, with increased proliferation of T cells. In addition, DCs mediate activation and proliferation of NK cells [Degli-Esposti and Smyth, 2005]. Trans binding of CLEC10a on DCs to a GalNAc residue on CD45 on T cells results in T cell inhibition [van Vliet et al., 2006]. Introduction of a GalNAc-containing factor frees CD45 and allows dephosphorylation (inactivation) of inhibitory receptors, removal of inhibitory phosphate groups from signal transduction kinases, and T cell activation. Inhibitory receptors that may be inactivated by CD45 signaling include CTLA-4 and PD-1.

Antibodies of the Combination Therapy

In addition to the foundational peptide regime, the combination therapy of the invention comprises an immunotherapy agent, for example, an antibody. In preferred embodiments of the combination therapy of the present invention, the antibody is a monoclonal antibody.

In some embodiments, the antibody is a monoclonal antibody against an immune checkpoint protein. Immune checkpoint blockade is a new and promising strategy to induce tumor regression, stabilize disease, and prolong survival by manipulation of the immune system [Weber, 2010]. Immune checkpoint proteins may be expressed by the T cell or by the antigen-presenting cell. T cell immune checkpoint proteins may be, for example, CTLA-4 and PD-1. Antigen-presenting cell immune checkpoint protein may be, for example, PD-L1 and PD-L2.

In one embodiment, the antibody is an antibody against CTLA-4 (α-CTLA-4). The use of the fully human, monoclonal antibody against CTLA-4, ipilimumab or Yervoy (Bristol Myers Squibb), has become a primary immunotherapeutic approach to cancer treatment. Studies in the mouse have demonstrated that T cells within a tumor have a high percentage of Treg cells, which have high expression of CTLA-4, and thus abrogate the immune response to the tumor cells. Introduction of α-CTLA-4 tags Treg cells and marks them for antibody-mediated destruction by macrophages. So α-CTLA-4 reduces the population of Treg cells.

In another embodiment, the antibody is an antibody against PD-1 (α-PD-1), which inhibits the interaction of PD-1 with its ligands to prevent inhibition of T cells. PD-1 is a member of the extended CD28/CTLA-4 family of T cell regulators [Ishida et al., 1992]. Monoclonal antibodies targeting PD-1 that boost the immune system have been developed for the treatment of cancer [Weber, 2010]. The FDA has granted accelerated approval to Keytruda (pembrolizumab; MK-3475), Merck's anti-PD-1 drug for advanced or unresected melanoma that no longer responds to other drugs. Melanoma is a skin cancer originating in pigment-producing cells called melanocytes. The disease is particularly swift and deadly in cases where it metastasizes to other sites in the body, particularly the brain. About 76,000 people will be diagnosed with melanoma in the U.S. this year and nearly 10,000 will die. Keytruda was intended for use after ipilimumab (Yervoy; Bristol-Myers Squibb), but currently is used clinically in combination with Yervoy, which blocks another T-cell receptor called CTLA-4 (see above). Bristol-Myers Squibb received approval in Japan for their α-PD-1 drug, Opdivo (nivolumab), leading to speculation that it might be the first to be approved in the U.S. Extensive studies have been performed to show durable tumor remission with nivolumab [Topalian et al., 2014].

The antibody may be an antibody against PD-1 ligands in another embodiment. PD-L1 and PD-L2, two ligands of PD-1, are members of the B7 family [Freeman et al., 2000; Latchman et al., 2001]. Many tumor cells express PD-L1, an immunosuppressive PD-1 ligand; inhibition of the interaction between PD-1 and PD-L1 can enhance T-cell responses in vitro and mediate preclinical antitumor activity. PD-L1 is expressed on almost all murine tumor cell lines, including PA1 myeloma, P815 mastocytoma, and B16 melanoma upon treatment with IFNγ. PD-L2 expression is more restricted and is expressed mainly by DCs and a few tumor lines. PD-L1 protein is up-regulated in macrophages and dendritic cells (DC) in response to lipopolysaccharide (LPS) and GM-CSF treatment and in T cells and B cells upon TCR and B cell receptor signaling [Iwai et al., 2002]. This response to LPS describes the critical reason for ensuring elimination of endotoxin from cancer therapeutic agents (see FIG. 4).

Clinical studies have shown that combinations of ipilimumab and nivolumab have greater efficacy than each alone [Curan et al., 2010; Wolchok et al., 2013]. Thus while the antibody of some implementations of the invention attacks one immune checkpoint pathway, the antibody of other implementations of the invention may attack more than one immune checkpoint pathway. For example, the combination therapy may comprise a peptide with antibodies against the CTLA-4 pathway and the PD-1 pathway, which are two distinct immune checkpoint pathways.

Kits or Pharmaceutical Compositions of the Combination Therapy

Because of the combination therapy comprises peptides that target regulatory lectin-type receptors and antibodies that directly affect the immune cells, the combination therapy of the present invention targets a combination of immune modulation avenues. For example, whereas the antibodies act by binding to checkpoint proteins on the cell surface, stimulation of phosphatase activity by CD45 and other phosphatases cause dephosphorylation of CTLA-4 and PD-1 and the accessory protein SHP-1 through which these proteins act, thus the combination therapy comprising the peptides of the invention and the antibodies also inactivate the inhibitory receptors from within the cell. However, the combination therapy of the present invention may target greater combinations of immune modulation avenues with the use of multiple peptides and/or multiple antibodies. Thus the combination therapy comprises a therapeutically effective amount of at least one peptide and a therapeutically effective amount of at least one antibody. In some embodiments, the peptide of the combination therapy has an active peptide sequence represented by SEQ ID NO:1 (VQATQSNQHTPR). The peptide may be tetravalent. The active peptide sequences of the tetravalent peptide is connected to the core by a linker sequence. In some embodiments, the core is a tri-lysine core and the linker sequence is -GGGS- (SEQ ID NO:2). An exemplary tetravalent peptide has the structure [(VQATQSNQHTPRGGGS)2K]2K—NH2 (SEQ ID NO:3).

In some embodiments of the kit or composition, the peptides are different mimetics that target the same regulatory lectin-type receptor. For example, in the case of a kit or composition comprising two peptides, both peptides target CLEC10a but each is a mimetic of either GalNAc or Gal. In other embodiments of the kit or composition, the peptides are different mimetics that target different regulatory lectin-type receptors.

In some embodiments of the kit or composition, the antibodies target different immune checkpoint pathways, for example, the antibodies target the CTLA-4 checkpoint pathway or the PD-1 checkpoint pathway. Thus the antibodies of the combination therapy may comprise α-CTLA-4 and one of α-PD-1 or α-PD-L1.

Pharmaceutically acceptable derivatives and salts thereof of the peptide and antibodies, and their use for the methods described herein are also within the scope of the present invention. Such salts may be prepared using knowledge in the pharmaceutical arts. Pharmaceutical compositions can be prepared in individual dosage forms. Consequently, pharmaceutical compositions and dosage forms of the invention comprise the active ingredients disclosed herein. The notation of "the pharmaceutical agent" signifies the compounds of the invention described herein or salts thereof. Pharmaceutical compositions and dosage forms of the invention can further comprise a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which an active ingredient is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, other excipients can be used.

The composition, shape, and type of dosage forms of the invention will typically vary depending on their route of administration and subject being treated. For example, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

For a particular condition or method of treatment, the dosage is determined empirically, using known methods, and will depend upon facts such as the biological activity of the particular compound employed, the means of administrations, the age, health and body weight of the host; the nature and extent of the symptoms; the frequency of treatment; the administration of other therapies and the effect desired. Hereinafter are described various possible dosages and methods of administration with the understanding that the following are intended to be illustrative only. The actual dosages and method of administration or delivery may be determined by one of skill in the art. Frequency of dosage may also vary depending on the compound used and whether an extended release formulation is used.

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, Natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103 and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an active ingredient, anhydrous lactose, microcrystalline cellulose, polyvinylpyrrolidone, stearic acid, colloidal anhydrous silica, and gelatin.

Methods of Administration

This invention also provides a method for administering the combination therapy of the invention where the peptide and the antibody are administered separately or in a formulation in which the combined drugs can be administered as a single application. For example, as in Example 8, the invention provides for the administration of svL4 and the monoclonal antibody α-CTLA-4 in a single application.

In one embodiment, administration of the combination therapy comprises starting the administration of the peptide at the same time as the antibody. In another embodiment, the combination therapy to activate the adaptive immune response is administered by first administering the peptide to prime the immune system before administering the antibody. For example, the peptide is administered at least two weeks, at least ten days, at least one week, at least five days, at least three days, or at least one day before the administration of the antibody. In some aspects, administration of the peptide is continued even after the administration of the antibody. Thus the administration of peptide is also concurrent to the course of administering the antibody. For example, iplimumab is usually injected intravenously every 3 weeks, so for the duration of the iplimumab treatment, the peptide is also administered.

In some implementations, administration of the peptide is continued after the period of antibody treatment. A benefit of this method is maintaining the therapeutic benefit of the antibody treatment even without subsequent treatment with the antibody.

The method of administering as well as the frequency and dose are established in the prior art for the antibody that is already FDA-approved. For example, ipilimumab is usually injected intravenously over a period of 90 minutes, and each unit dose is given every three week with a single course being up to four doses. However, in some aspects, the concurrent administration of the peptide and the antibody may be at a frequency of every week.

The unit dosage of the peptide may be administered on alternate days or on a weekly basis. Single unit dosage forms of the peptide of the invention are suitable for oral, mucosal (e.g., nasal, sublingual, vaginal, buccal, or rectal), parenteral (e.g., subcutaneous, intravenous, bolus injection, intramuscular, or intra-arterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. The peptide is preferably administered via a parenteral route, most preferably, the subcutaneous route. The peptide can also be administered intravenously. The peptide may be administered alone or in a composition with the antibody.

In certain aspects, the peptide may be administered in unit dosage amounts of about 0.1 nmol/kg body weight to about 1500 nmol/kg body weight, which corresponds to about 0.7 µg/kg body weight to about 10 mg/kg body weight. The unit dosage of the peptide may also be about 100 nmol/kg body weight to about 1500 nmol/kg body weight, about 100 nmol/kg body weight to about 1000 nmol/body weight, about 3 nmol/kg body weight to about 1500 nmol/kg body weight, about 3 nmol/kg body weight to about 1000 nmol/kg body weight, about 3 nmol/kg body weight to about 10 nmol/kg body weight, about 1 nmol/kg body weight to about 1000 nmol/kg body weight, or about 0.1 nmol kg body weight to about 1 nmol kg body weight.

In other aspects, the peptide may be administered in a unit dosage amount of less than about 1500 nmol/kg body weight, for example, about 1000 nmol/kg body weight, about 500 nmol/kg, about 100 nmol/kg, about 10 nmol/kg, about 1 nmol/kg, or about 0.1 nmol/kg. In one aspect, the peptide may be administered in unit dosage amounts of about 5 nmol, about 10 nmol, about 15 nmol, about 25 nmol, about 30 nmol, about 50 nmol, about 75 nmol, about 100 nmol, about 225 nmol, about 250 nmol, about 500 nmol, about 750 nmol, about 1 µmol, about 10 µmol, or about 50 µmol.

Parenteral dosage forms can be administered to patients by various routes including, but not limited to, subcutaneous, intravenous, bolus injection, intramuscular, and intraarterial. Preferably the parenteral dosage form is suitable for subcutaneous delivery. The parenteral dosage forms of the invention are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: water for Injection USP; aqueous vehicles such as, but not limited to, phosphate-buffered saline, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Examples

The present invention is further illustrated by the following examples that should not be construed as limiting. The contents of all references, patents, and published patent applications cited throughout this application, as well as the Figures, are incorporated herein by reference in their entirety for all purposes.

1. svL4, an Exemplary Peptide of the Invention

Figure 2:
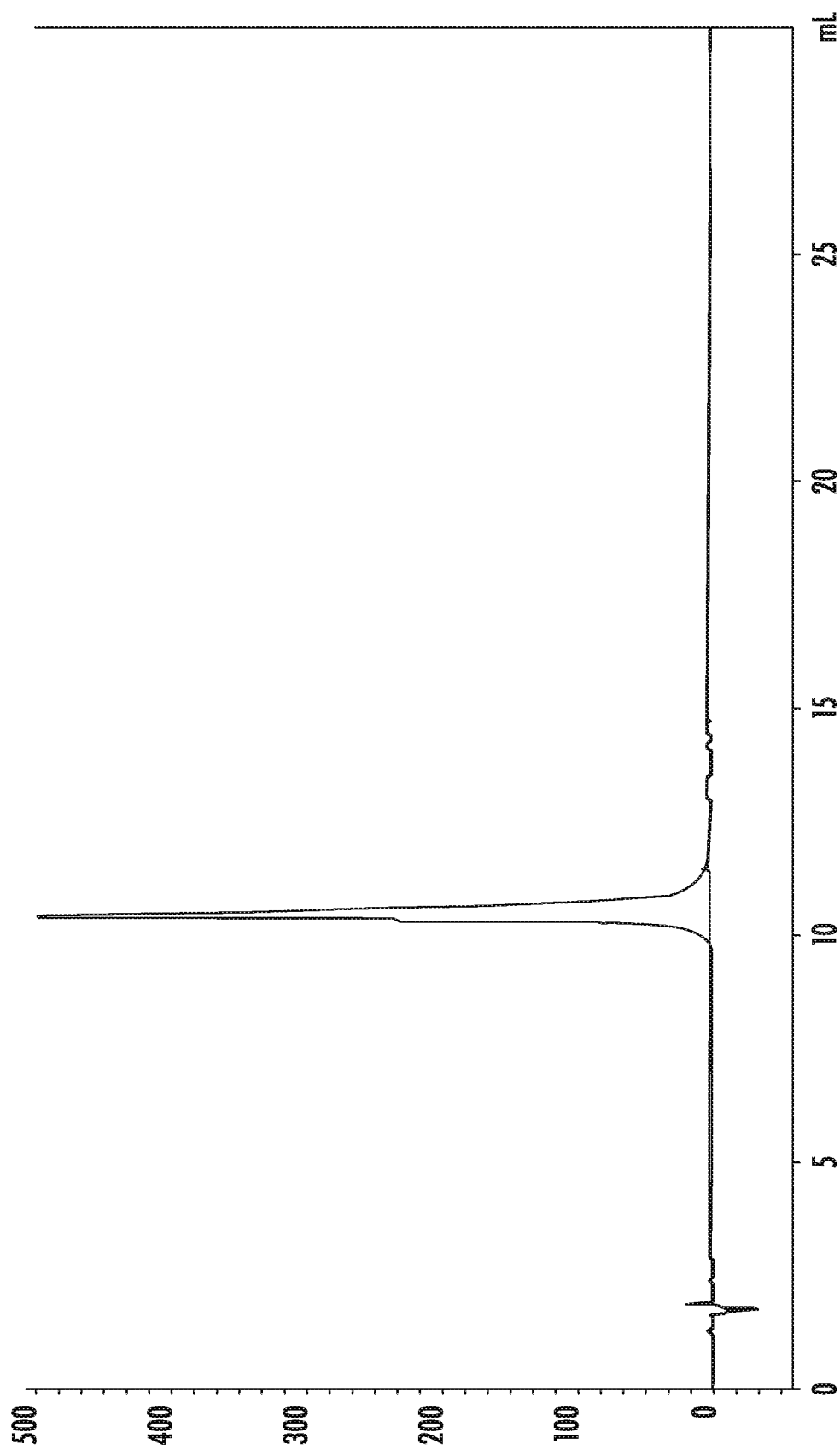
FIG. 2 depicts HPLC trace of svL4. Chromatography was performed by CBL with a C8 column with a gradient of acetonitrile in 0.1% TFA/water. Purity of the peptide is >95%.
Figure 3:
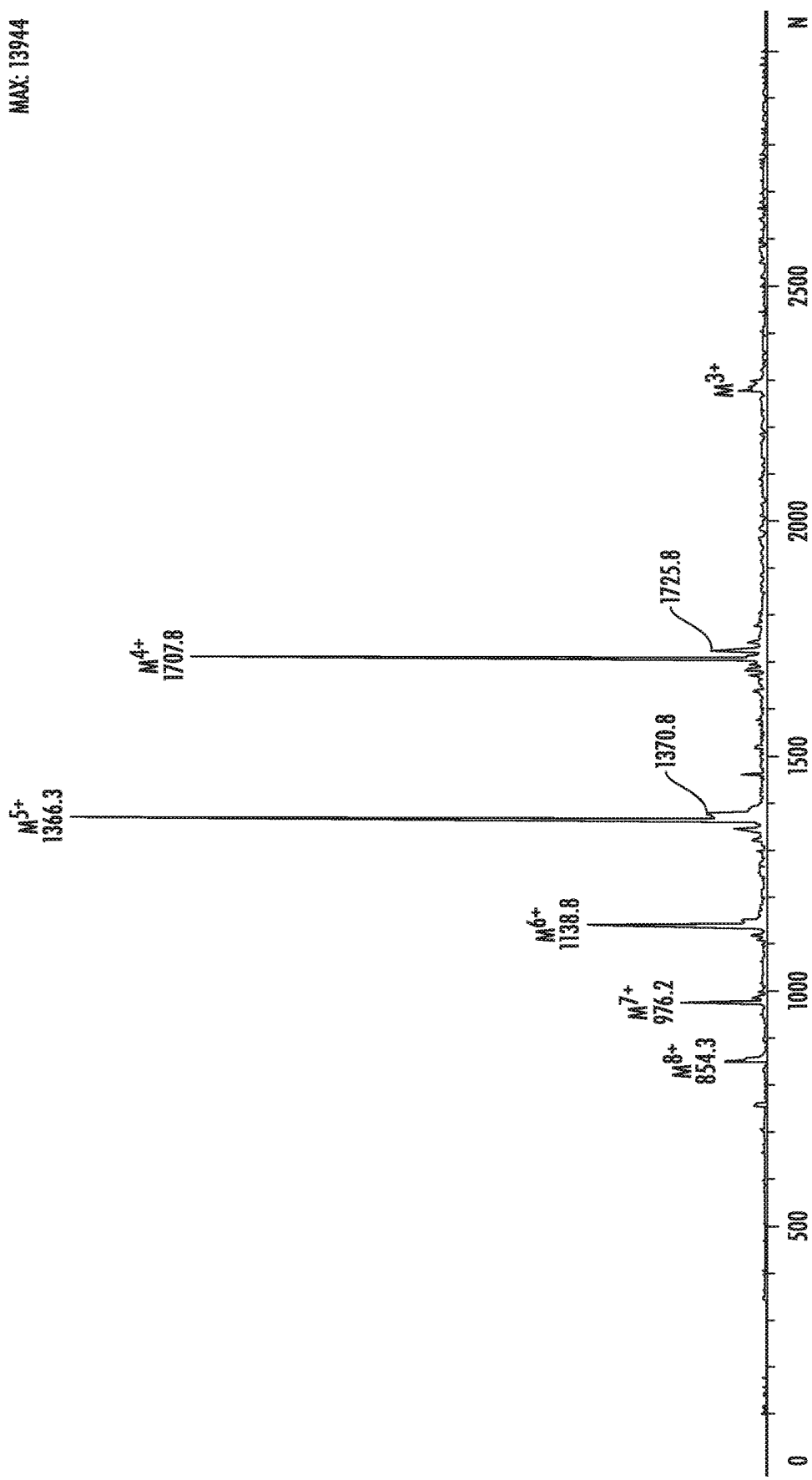
FIG. 3 depicts electrospray ionization (ESI) mass spectrum of svL4. Ionization state of the peptide for each signal is indicated.
Figure 4:
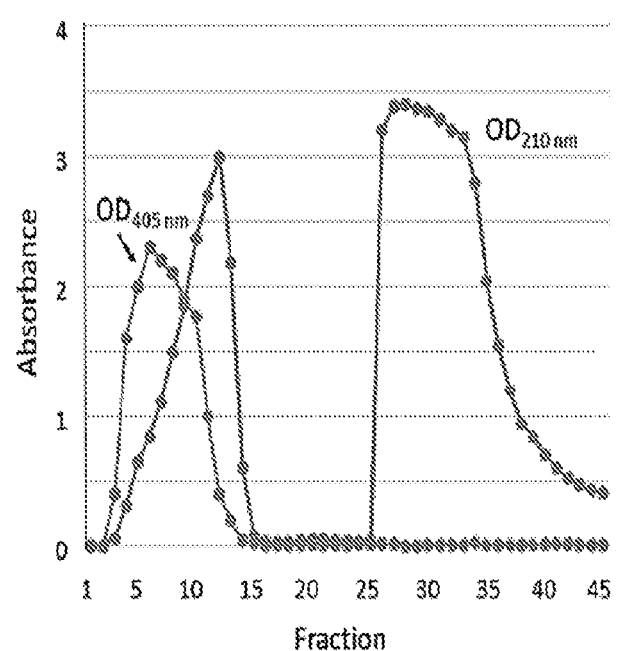
FIG. 4 depicts elution of svL4 from a column of CM-Sephadex C50. svL4 was passed through a column of DEAE-Sephadex A25 in 25 mM NaCl. The concentration of NaCl was then raised to 100 mM and the sample was applied to the CM-Sephadex column. The column was washed with 25 mL 100 mM NaCl, then with 50 mL 200 mM NaCl, and then with 500 mM NaCl, beginning at fraction 24. Fractions (1:100 dilution) were monitored by OD at 210 nm for peptide content and at 405 nm for endotoxin by the Limulus amebocyte lysate (Lonza, Walkersville, Md., USA) colorimetric assay method.

A peptide mimetic of GalNAc, designated svL4, was found in a screen of a phage display library with the GalNAc-specific lectin from *Helix pomatia* [Eggink and Hoober, 2009, 2010]. The tetravalent form of the peptide has the structure [(VQATQSNQHTPRGGGS)$_2$K]$_2$K—NH$_2$ (SEQ ID NO:3, FIG. 1). The peptide was synthesized by standard solid-phase chemistry and prepared endotoxin-free at >95% purity by chromatographic procedures (FIGS. 2-4).

2. The Binding Activity svL4 to Human Lectin-Type Receptors

Figure 5:
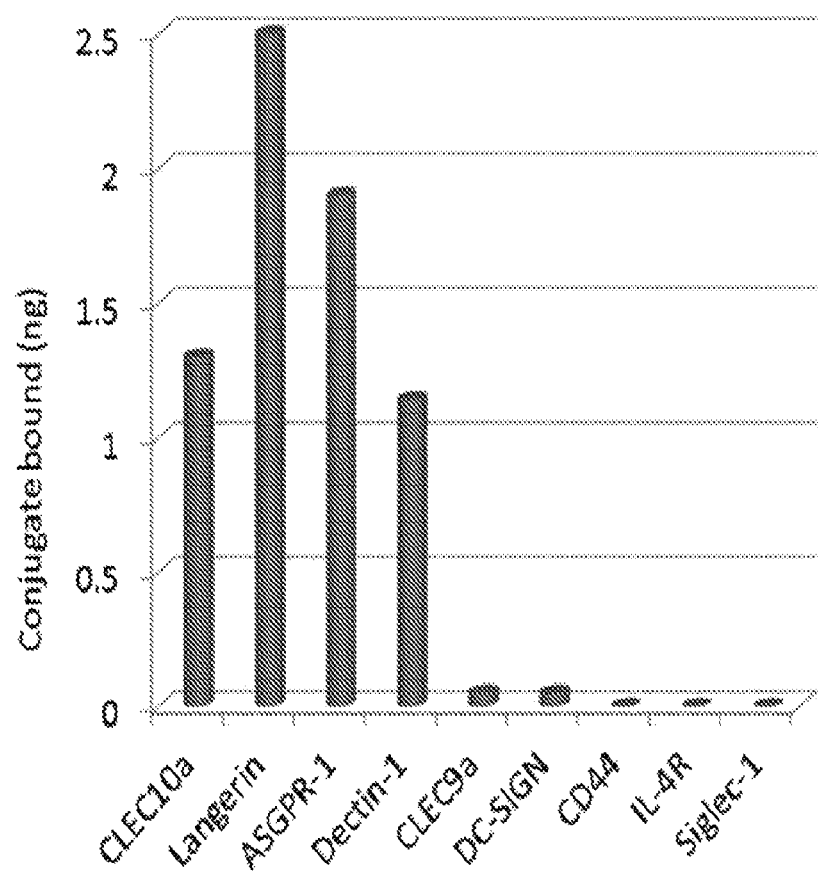
FIG. 5 depicts the binding activity of svL4 to (left-to-right) CLEC10a, Langerin, ASGPR1, Dectin-1, CLEC9a, DC-SIGN, CD44, IL-4R, and Siglec-1.

The binding activities of svL4 were determined for recombinant human CLEC10a, ASGPR1, and Langerin. FIG. 5 presents the binding activities of svL4 to various regulatory lectins. Of the lectins tested, svL4 binds strongly to CLEC10a, Langerin, ASGPR-1, and Dectin-1.

Figure 6:
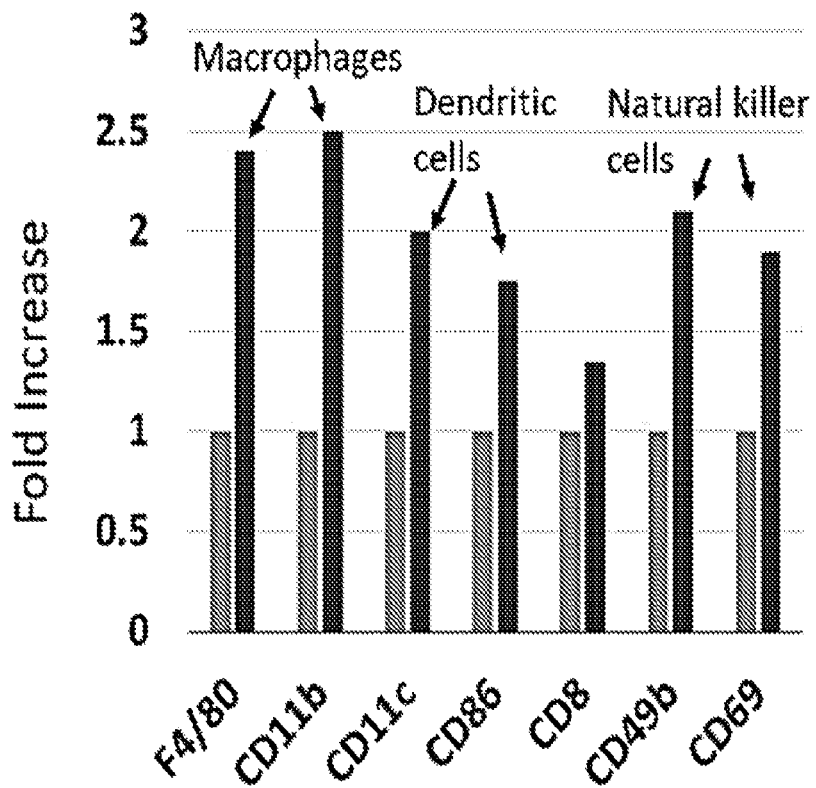
FIG. 6 depicts fold increase in the high-staining populations for the markers on peritoneal cells from C57BL/6 mice dosed Q2D with 1 nmol/g svL4. Untreated values were normalized to 1.0 (grey bars) to show fold increase with svL4 administration (black bars) and to compare responses between cell types at day 3 of treatment.

3. Effect of svL4 Group of Peptides on Maturation of Immune Cells in Wild-Type Mice To examine maturation of peritoneal immune cells, mice (strain C57BL/6, male, 6-8 weeks old) were given subcutaneous injections of 1 nmol/g tetravalent svL4 on days 0, 2, 4 and 6. Expression of biomarkers with cells stained with antibodies against the markers is shown in FIG. 6. Dramatic changes occurred in cells obtained from the peritoneal cavity of these animals, a major site of immune function. Maturation of immune cells was found in several populations of cells after two treatments as illustrated in FIG. 6, which showed an increase in highly stained cells in treated C57BL/6 mice at day 3. Thus subcutaneous administration of svL4 enhances maturation of immune cells in the peritoneal cavity.

Increases were found in populations stained with antibodies against CD11c (dendritic cells), which is up-regulated on most activated antigen presenting cells (dendritic cells, macrophages, and B cells). The population of macrophages (F4/80$^+$CD11b$^+$) cells increased dramatically during the initial 3 days of treatment. The number of dendritic cells (CD11c$^+$) and activated dendritic cells also were elevated. CD8$^+$ cells were slightly elevated, and CD49b$^+$CD69$^+$ (active) NK were strongly elevated. Shown in FIG. 6 are the changes at day 3 with injections on alternate days.

Figure 7:
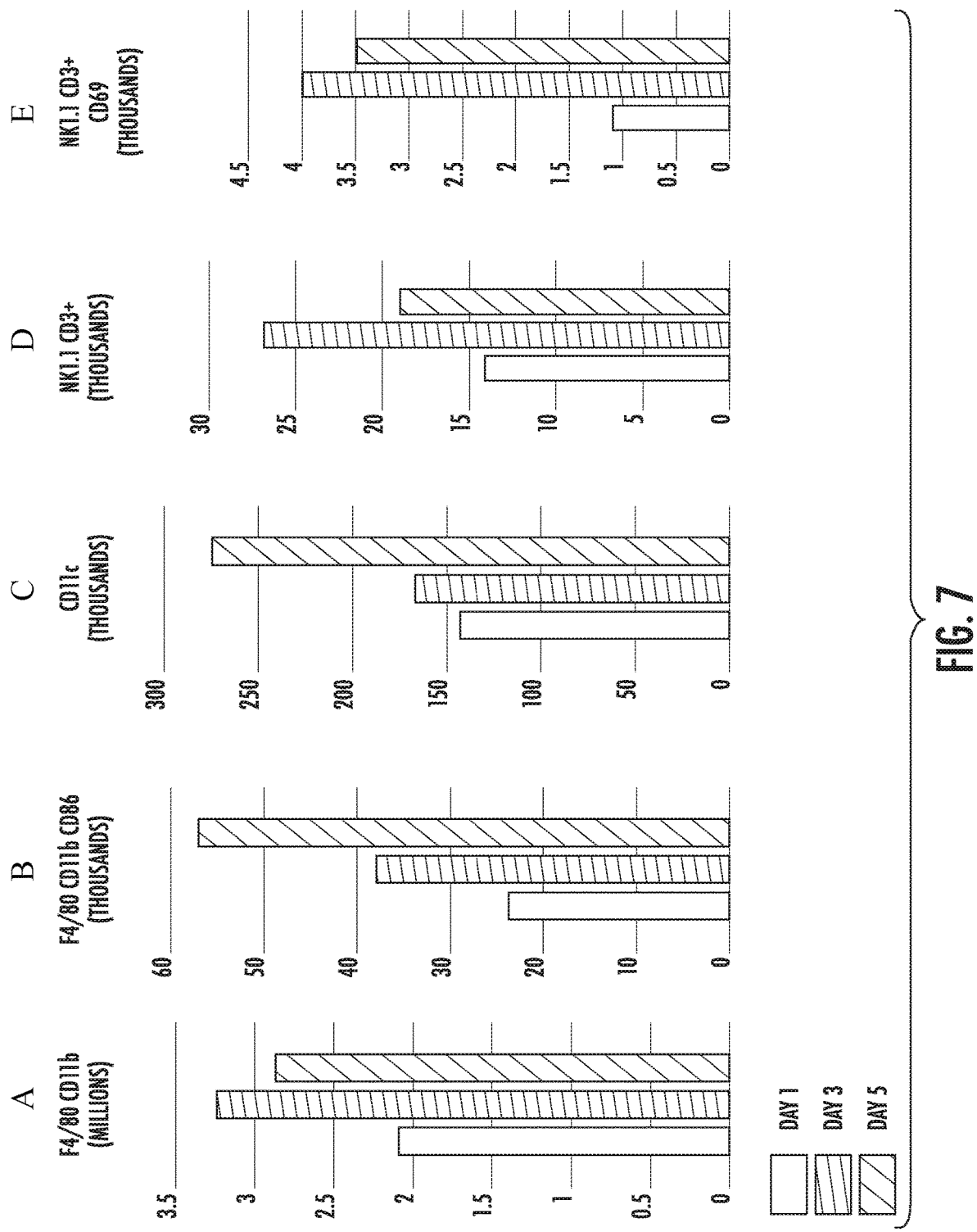
FIG. 7 depicts the increases in peritoneal cell types found in C57BL/6 mice treated with 1 nmol/g svL4 in a time course experiment. For each cell type, the three bars in each group indicate data from day 1, day 3, and day 5, i.e., one day after each subcutaneous injection on day 0, day 2 and day 4. Cell numbers of macrophages (F4/80 CD11b) are indicated in panel A, activated macrophages (F4/80 CD11b CD86) in panel B, DCs (CD11c) in panel C, NKT cells (NK1.1 CD3$^+$) in panel D, activated NKT cells (NK1.1 CD3$^+$ CD69) in panel E, activated NK cells (NK1.1 CD3$^-$ CD69) in panel F, activated Th cells (CD4 CD69) in panel G, cytotoxic T cells (CD8 CD69) in panel H, B cells (CD19) in panel I, and of B memory cells (CD19 CD73 CD80 CD273) in panel J. The data are expressed as actual cell counts in the analyses.
Figure 7:
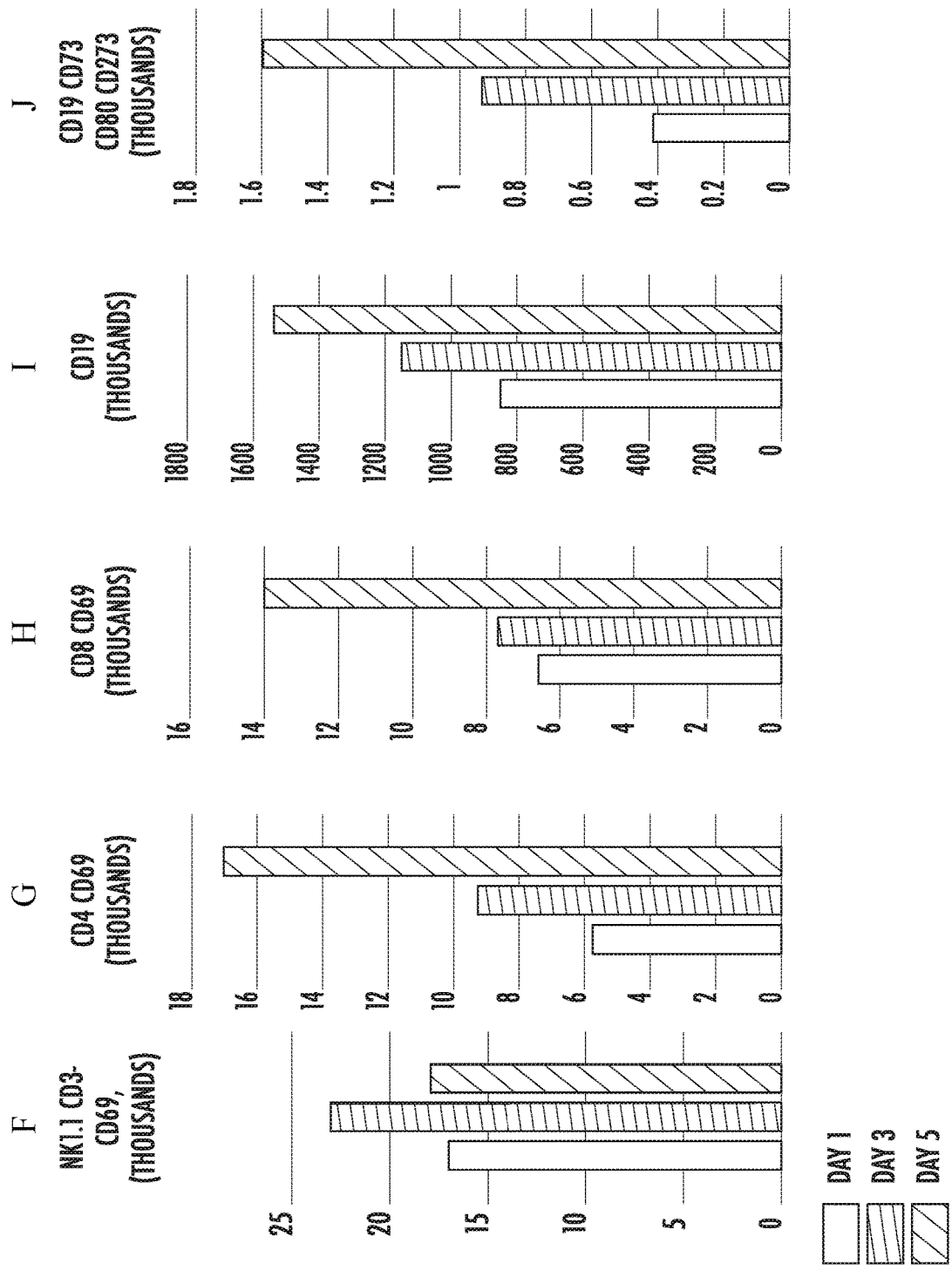

In a second experiment, the time courses of changes in additional cell populations were examined, which included macrophages (F4/80 CD11b), activated macrophages (F4/80 CD11b CD86, DCs (CD11c), NKT cells (NK1.1 CD3+), activated NKT cells (NK1.1 CD3+ CD69), activated NK cells (NK1.1 CD3− CD69), activated Th cells (CD4 CD69) cytotoxic T cells (CD8 CD69), B cells (CD19), and of B memory cells (CD19 CD73 CD80 CD273). The responses, represented by the number of each cell type over 5 days with alternate-day injections, are depicted in FIG. 7.

4. Effect of svL4 on Serum of Mice Bearing Breast Cancer Tumors

To determine whether the responses in serum proteins would be different in tumor-bearing mice from those in healthy mice, sera were collected from female mice in which breast cancer 4T1 cells had been implanted. After the tumors had grown over a period of 10 to 12 days to a size of ~500 mm$^3$, tetravalent svL4 was injected subcutaneously at doses of 0.1 and 1.0 nmol/g. Blood was withdrawn and sera prepared 4 hours after injection. The sera of untreated animals had low levels of cytokines and chemokines at 4 h. Factors that reflect activation of typical immune cells are listed in Table 1. With a few proteins, such as IL-1β, IL-2, IL-6 and TNFα, the values were very low in untreated animals and upon treatment with svL4 were increased but still nearly undetectable on the array blots. Treatment generally resulted in increases with many of the proteins, typically in the range of 3- to 5-fold. Several cytokines that increased but were still low in amount included GM-CSF, CCL4, IGFBP-1, IL-21, lymphotoxin-α, and IL-17. Major proteins included CCL1, CCL8, CCL28, Endostatin, Fas, HVEM, IL-11, IL-12p70, IL-16, IL-27, IL-28, MIP-2, MMP-9, NOV, Soggy-1, SPARC, TIMP-2, TLR2 and VEGF-B. In some cases, the higher dose caused a higher amount of the protein, whereas with several proteins the amount was lower with the higher dose. With most cytokines, the extent of changes suggested dose-dependent responses in this range. A number of soluble proteins were identified as cell-surface receptors, such as Fas, HVEM and TLR2, which indicated significant shedding by activated cells. Soluble HVEM was a major protein in tumor-bearing mice, as in healthy mice, but the level in control mice was greater in mice with breast cancer, which led to only a 2-fold increase after treatment with svL4.

TABLE 1

Markers of lymphocyte and monocyte activation in response to svL4 in Balb/c mice bearing breast tumors compared with healthy mice.

| Cytokine | Fold increase in treated vs. untreated mice | Expression | Healthy Balb/c |
|---|---|---|---|
| Maximum at 0.1 nmol/g svL4 | | | |
| IL-2 | 56 | T cells | High* |
| IL-15 | High* | Mononuclear phagocytes | High* |
| IL-17 | High* | T helper cells | No change |
| IL-23 | High* | Dendritic cells and macrophages | 0.55 |
| IL-27 | 4.5 | Antigen-presenting cells, promotes Th1 responses | High* |
| IL-28 | 4.3 | Augments IFNγ release, cytotoxic potential for CD8+ T cells | High* |
| IL-31 | 3.5 | Activated Th2 T cells | High* |
| MIP-2/CXCL2 | ~6 | Secreted by monocytes and macrophages | No change |
| Pentraxin3 | ~4 | Mononuclear phagocytes, dentritic cells, and neutrophils | 0.21 |
| SPARC | ~5 | Osteoblasts, macrophages at site of wound repair | No change |
| TIMP-2 | 2.9 | Monocytes and placenta (metastasis suppressor) | 0.45 |
| TNFα | 4.6 | Activated monocytes and macrophages | 0.2 |
| TLR2 | 4.2 | Activated monocytes, dendritic cells, macrophages, and B and T cells | 0.37 |
| Lymphotoxin-α | 12.5 | Th1 T cells | 0.74 |
| Maximum at 0.1 and 1 nmol/g svL4 | | | |
| IL-16 | 4 | Released by lymphocytes | 0.57 |
| sHVEM | ~2 | Activated monocytes and lymphocytes (healthy control mice had lower level) | 5 |
| Maximum at 1 nmol/g svL4 | | | |
| IFNγ | High* | Primarily activated lymphocytes | No change |
| CCL1 | 2.5 | Activated T cells | No change |
| CCL8/MCP-2 | 5 | Induced by IFNγ | High* |
| IL12p70 | 3.5 | Dendritic cells and macrophages | No change |
| IL-21 | High* | Activated CD4+ cells | No change |

*In these samples, the control value was negligible, thus the fold increase in treated samples when the amount was detectable, even though very low, appeared high.

These proteins are expressed by a variety of cell types, including activated CD4+ and CD8+ T cells, dendritic cells, and macrophages, and are nearly all involved in regulation of the immune system. The pattern of expression of cytokines/chemokines provides a strong anti-cancer immune response. Of particular note, although a large number of cytokines and chemokines increase in the serum in response to treatment, a pattern typical of a toxic "cytokine storm" did not occur.

Significant differences were observed between serum proteins from healthy and tumor-bearing mice. Whereas in healthy mice, IL-16, MMP-9, P-selectin, Soggy-1, TLR2, TRAIL, and TIMP-2 decreased, these factors increased dramatically in tumor-bearing mice in response to svL4. IL-1α, IL-6, IFNγ, TNFα and TGFβ, which were present at very low levels and did not increase in healthy mice, were detectable in tumor-bearing mice and increased significantly in response to svL4. Additional comparisons are shown in Table 1. The far-right column of Table 1 shows the ratio of treated (1 nmol/g) vs. untreated samples obtained in a separate experiment with healthy Balb/c mice. Several proteins, in particular IL-15, IL-17, IL-21, IL-28, IL-31 and CCL8/MCP-2 had negligible values in untreated mice, and thus the treated value had a high ratio. Interestingly, cytokines that were strongly elevated in mice bearing tumors were often reduced in healthy mice in response to svL4 or showed no change.

5. Treatment of Melanoma with svL4 and α-CTLA-4

Research has demonstrated that α-CTLA-4 is ineffective against melanoma in the mouse unless a source of GM-CSF was added, which routinely was provided by injection of irradiated, engineered GVAX cells [Quezada et al., 2006]. Whereas the inhibitory receptor, CTLA-4, was expressed at high levels by Treg cells within tumors, destruction of cells with bound α-CTLA-4 required macrophages that expressed FcγRIV [Simpson et al., 2013]. Because administration of svL4 causes proliferation and maturation of monocytes, we tested whether svL4 could replace GM-CSF. For this experiment, male C57BL/6 mice were implanted on their right flank with $1.5 \times 10^5$ B16 tumor cells. Subcutaneous injections of 1 nmol/g tetravalent svL4 were initiated on day 0 and given Q2D throughout the experiment. Intraperitoneal injections of 100 μg α-CTLA-4 monoclonal antibody (clone 9H10 from BioXCell) were given Q3D starting on day 3. Combination treatment retained these injection frequencies.

Tumor growth was measured on alternate days. Most rapid increases in tumor volume occurred within the group treated with α-CTLA-4 alone, whereas the slowest increases occurred in the group treated with α-CTLA-4 with 1 nmol/g tetravalent svL4 (Table 2).

TABLE 2

Volume of melanoma tumors on day 11.

| Group | Mean volume (mm$^3$) | Std. Dev. | SEM | n |
|---|---|---|---|---|
| Control | 455 | 613 | 204 | 9 |
| svL4, 1 nmole/g | 201 | 95 | 39 | 6* |
| α-CTLA-4 | 680 | 825 | 292 | 8 |
| α-CTLA-4 + svL4 | 137 | 91 | 32 | 8 |

(*Animals in this group were euthanized because of injuries from fighting).

Figure 8:
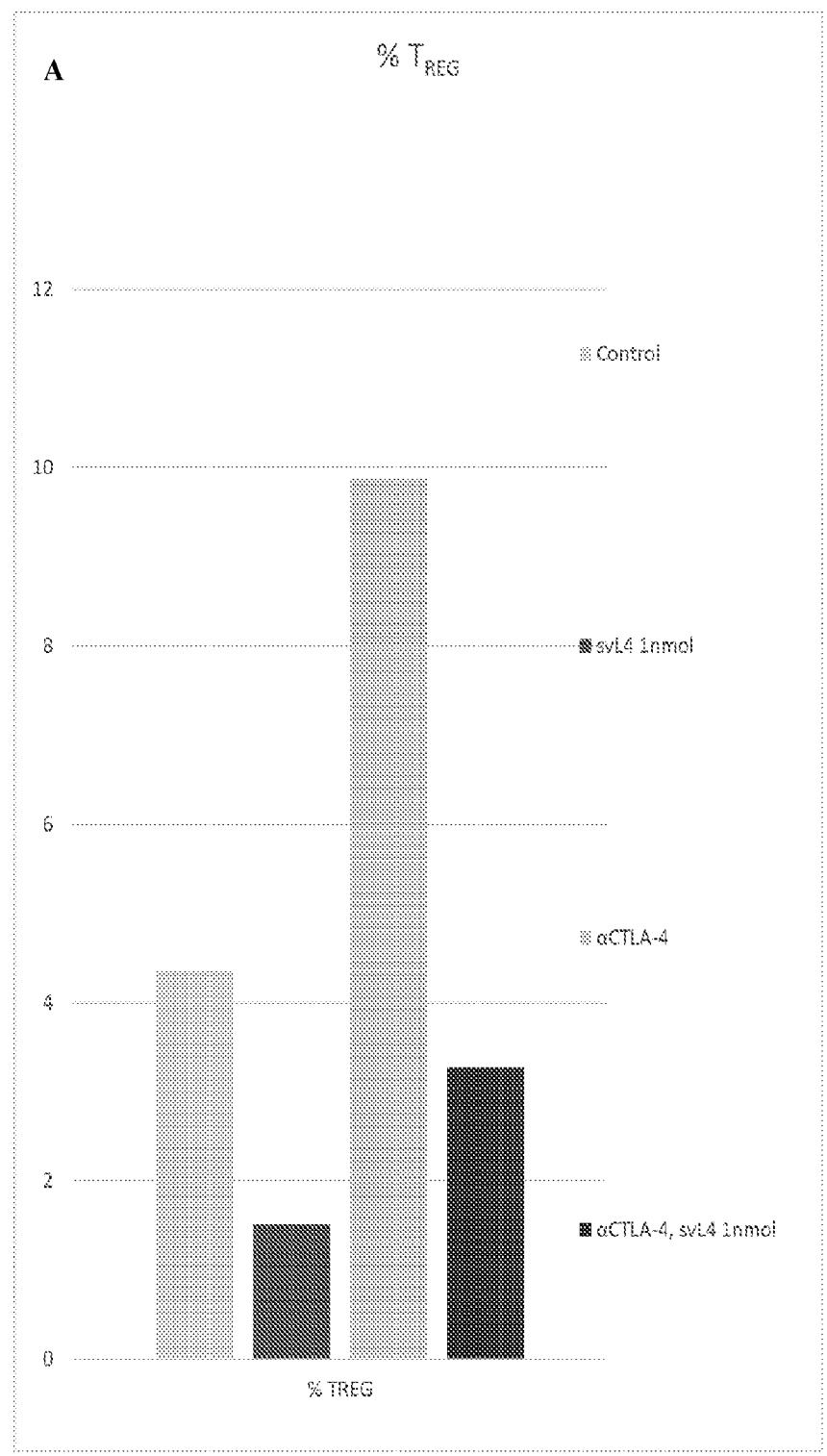
FIG. 8 depicts the percent Treg cells in dissociated B16 melanoma tumors (A) and the ratio of effector T cells to regulatory T cells in tumors (B). svL4 was administered subcutaneously on alternate days at a dose of 1.0 nmol/g body weight. Antibody against cytotoxic T-lymphocyte associated molecule-4 (α-CTLA-4) was injected intraperitoneally every third day at a dose of 100 µg per animal. The bars show averages of two flow analyses.
Figure 8:
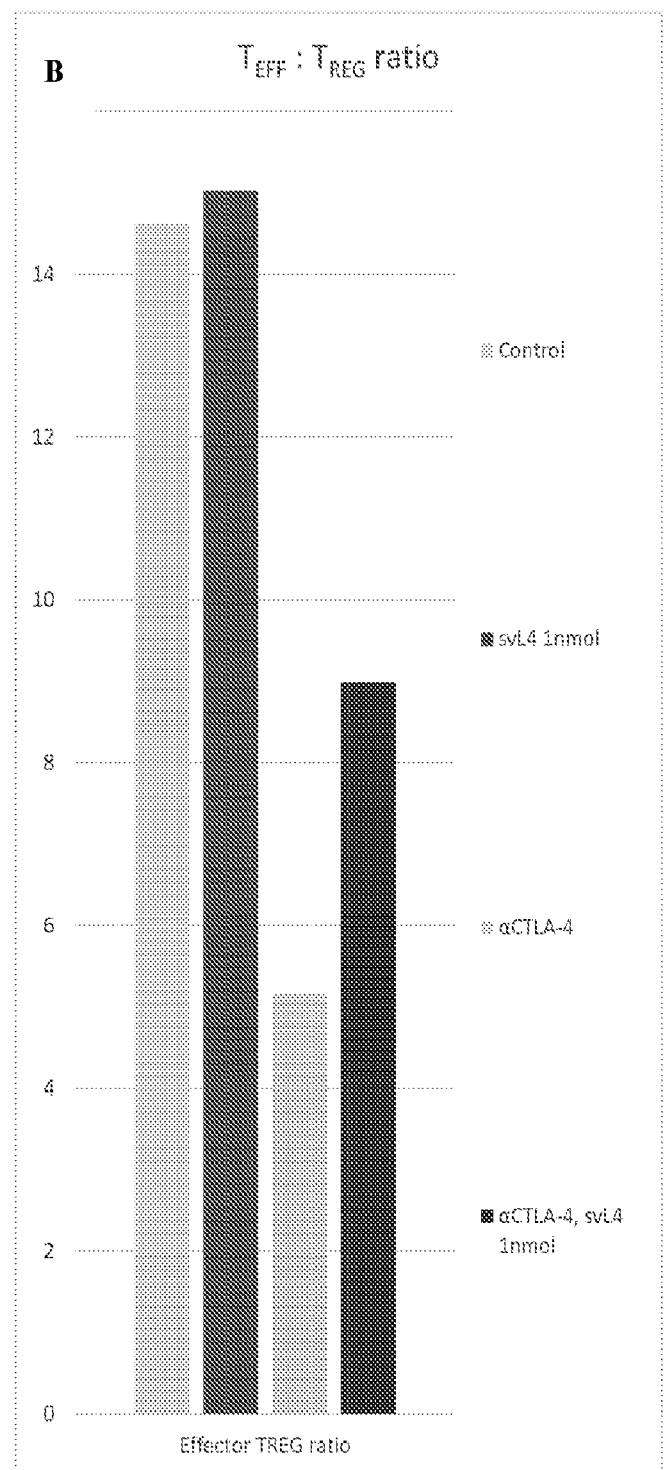
Figure 9:
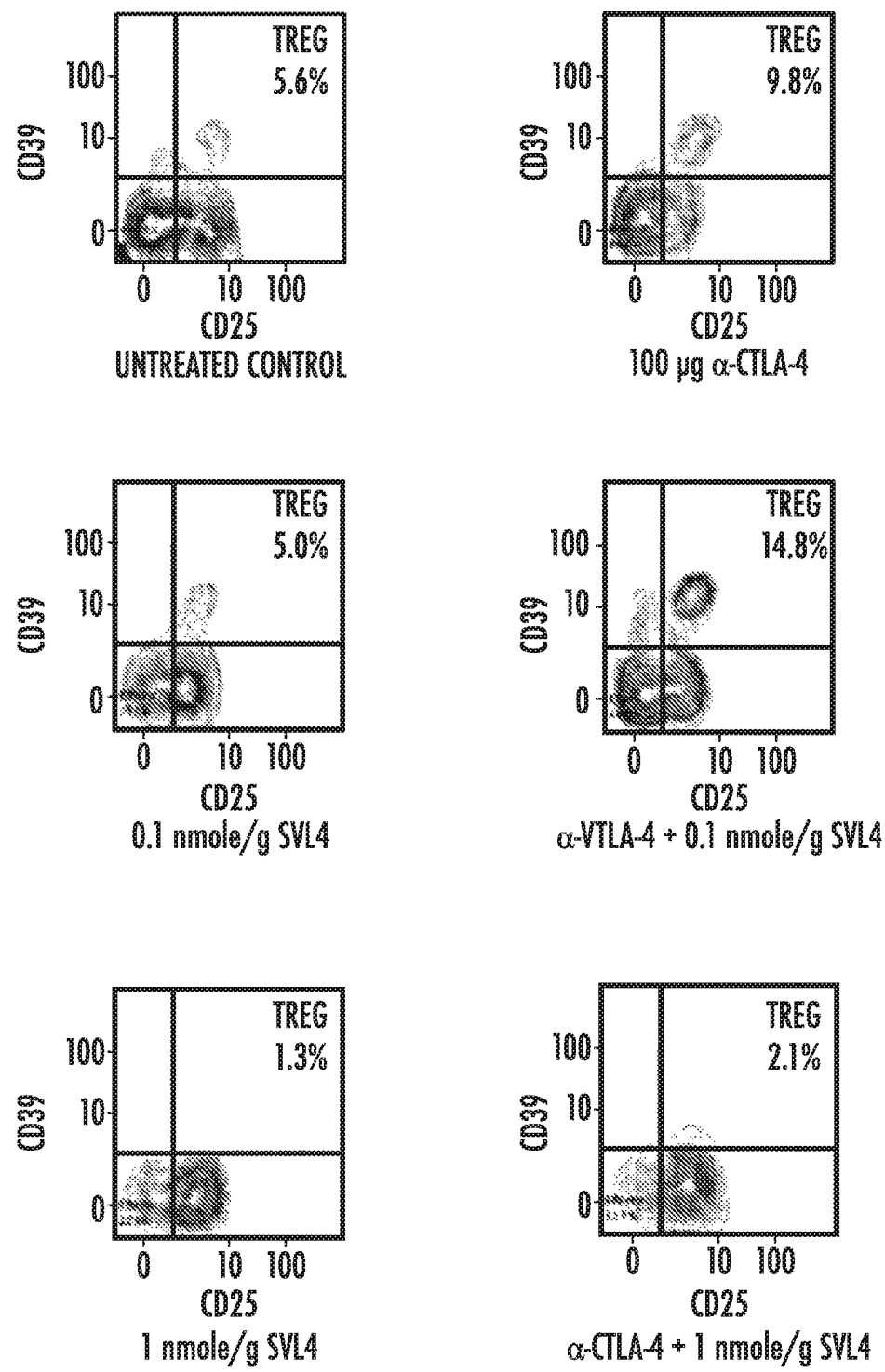
FIG. 9 depicts flow analyses of tumor cells from animals implanted with B16 melanoma cells and the treatments each animal received as described in the legend to FIG. 8.

When the majority of the tumors in the untreated group reached a maximum volume of 1,500 mm$^3$, the mice were sacrificed and primary tumors from two representative animals from each group were excised and analyzed by flow cytometry. Effector T (Teff) cells were defined as CD3$^+$CD4$^+$CD25$^-$CD39$^-$ while Treg cells were defined as CD3$^+$CD4$^+$CD25$^+$CD39$^+$ [Dwyer et al., 2010]. Uncharacterized CD25$^+$/CD39$^-$ and CD25$^-$/CD39$^+$ cells were excluded from the Teff:Treg calculation. A summary of the T cell analyses is shown in FIG. 8. (Examples of the flow cytometry data plots are shown in FIG. 9). The lowest percentage of Treg cells among the total T cell population occurred in tumors from animals treated with 1 nmol/g svL4 alone (FIG. 8A). Interestingly, the highest percentage among the treated groups occurred in animals treated α-CTLA-4. Addition of 1 nmol/g svL4 to the treatment with α-CTLA-4 dramatically reduced the percentage of Treg cells. Likewise, the highest ratio of Teff:Treg cells among treated groups was found with 1 nmol/g svL4 alone (FIG. 8B).

The data indicate that 1 nmol/g svL4 complemented the activity of α-CTLA-4 by reducing the population of Treg cells. In effect, svL4 decreased the number of Treg cells by an α-CTLA-4-independent mechanism. A possible explanation for the strong antibody-independent decrease in Treg cells is provided by cytokine data with sera from Balb/c mice bearing breast cancer tumors (Table 1). svL4 induced a several-fold increase in IL-12p70, IL-21 and IL-27 within 4 h. These cytokines are implicated in suppression of Treg cell proliferation and a decrease in IL-2 receptor expression [Zhao et al., 2012]. svL4 did not induce an increase in IL-10, an inhibitory cytokine secreted by Treg cells. In clinical studies, the decrease in Treg cells appears more significant for a positive therapeutic outcome than the Teff:Treg ratio [Sim et al., 2014]. Thus, the decrease in Treg cells in the groups treated with svL4, along with maturation of macrophages, dendritic cells, CD8$^+$ cytotoxic T cells and natural killer cells that we observed in response to svL4 administration (FIG. 6), would support a powerful enhancement of the immune system's attack on cancer.

The data show that svL4 alone and in combination with α-CTLA-4 have primary roles in the reduction of immunosuppressive regulatory T cells in tumors. The data suggest that the two factors have separate but complementary activities. The hypothesis thus arises that such a treatment should be appropriate for a variety of cancers. Indeed, α-CTLA-4 is currently being tested in Phase II and III trials in melanoma, and in Phase I/II trials in other tumor types. Evidence of tumor regression and durable responses has been observed with the monoclonal ipilimumab in patients with ovarian cancer, prostate cancer and renal cell cancer [Weber, 2010]. Antibodies against CTLA-4 are more effective against cancers in humans than in the mouse. svL4 is effective in the mouse and is also expected to be effective in humans. Antibodies against CTLA-4 (ipilimumab) are effective in only 20 to 30% of patients, and efficacy is approximately doubled when combined with nivolumab, an antibody against another checkpoint marker PD-1 [Wolchok et al., 2013]. These combinations have increased efficacy because they target different inhibitory receptors. Thus, based on data from the mouse study of melanoma, addition of svL4 to a treatment with α-CTLA-4, α-PD-1, or α-PD-L1 should enhance benefit. The invention satisfies the need expressed by oncologists for a non-toxic backbone or foundational therapy that activates a range of cells and 'primes' the immune system. These checkpoint blockade antibodies then can provide focused therapies at lower doses and with less toxicity.

Treatment of cancer is usually begun after diagnosis, which is often at the point of advanced disease. To provide an initial activation of the immune system, svL4 is given on alternate days by subcutaneous injection. Activation of immune cells is detected in the mouse after the second or third injection, i.e., day 3 or 5 after the start of treatment. Ipilimumab is usually injected intravenously every 3 weeks. The continued alternate day administration of svL4 would maintain the immune system at an elevated state of activation and thus establish conditions for the immune system to achieve maximal benefit from the injections of α-CTLA-4. A similar method should be feasible with α-PD-1.

6. Treatment of Glioblastoma with svL4

Massive infiltration of regulatory T (Treg) cells was found in glioblastoma and metastatic brain tumors, which efficiently suppressed cytokine secretion and proliferation of effector lymphocytes [Joannes et al., 2009]. Most malignant cells expressed PD-L1 while PD-1 was expressed on a subset of T effector cells. To test whether svL4 would show efficacy against brain tumors, mice (strain C57BL/6, female, 6-8 weeks old) were implanted with glioma cells (murine GL261 cell line) into one hemisphere of the brain. After a period of one week to allow a tumor to develop, tetravalent svL4 was injected subcutaneously at a dose of 1 nmol/g on alternate days for two weeks [Kushchayev et al., 2012a, 2012b].

Survival of mice (strain C57BL/6, female, 6-8 weeks old) with implanted glioma cells (murine GL261 cell line) was determined after treatment with radiation (4 Gy on day 7 and 9) alone, peptide (1 nmol/g) alone on alternate days beginning on day 7, or radiation plus peptide. As shown in FIG. 10A, the size of the tumor was slightly reduced in peptide-treated animals but life of the animals was not significantly extended (Table 3). However, in conjunction with radiation, the peptide dramatically extended life, with a two-fold increase from the start of treatment (FIG. 10B). These results suggest that activated phagocytic cells in the brain cannot effectively attack a solid tumor, although the tumor seemed to initially expand by invasion of phagocytic cells. After radiation, the tumor cells apparently were damaged sufficiently to allow their destruction by phagocytes, which was indicated by the marked reduction in tumor size. The minimal size of the tumor at day 19 with combined therapy suggests that tumor growth was delayed, a significant indicator of clinical potential [Teicher, 2006].

TABLE 3

Figure 11:
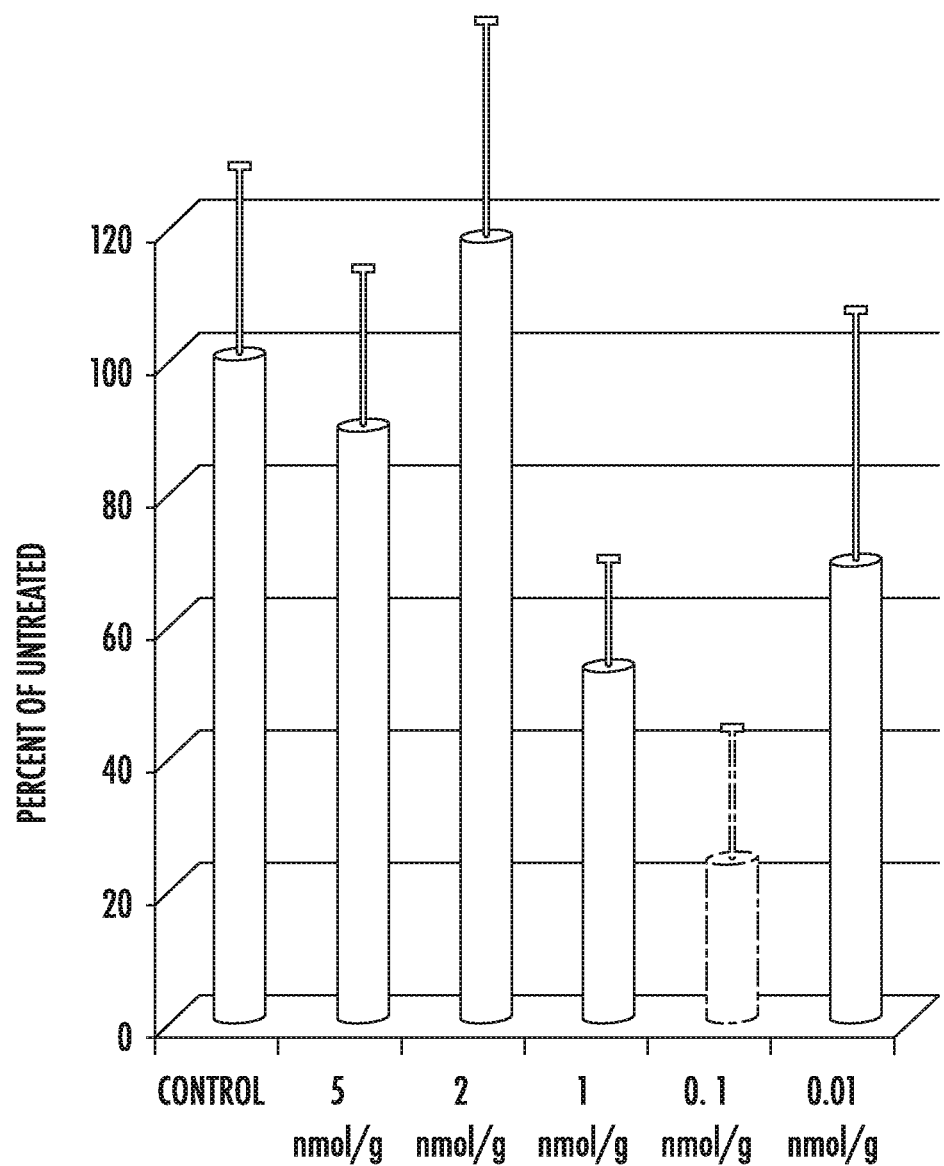
FIG. 11 depicts a study of the effect of dose of svL4, given subcutaneously on alternate days, on tumor size in mice implanted with glioma cells in the brain. Treatment was with peptide alone in this experiment. Tumor size is expressed as a percent of the tumor in untreated control mice.

Median survival of mice in the experiment shown in FIG. 11.

| Treatment | Survival after implantation (days) |
|---|---|
| Control (sham injection of saline) | 21 |
| svL4 (1 nmol/g, administered on alternate days) | 22 |
| Radiation (2 treatments of 4Gy each) | 30 |
| svL4 + Radiation | 38 |

7. Dose Response Study of svL4

In most of our experiments with mice, tetravalent svL4 was administered routinely at a dose of 1 nmol/g on alternate days, which we consider to be a maximal effective but not necessarily the optimal dose. In other experiments we found greater effectiveness at doses of 0.1 to 0.2 nmol/g (0.68 to 1.4 mg/kg). In an experiment with mice into which glioma cells were implanted in the brain, a dose of 0.1 nmol/g alone on alternate days was more effective in causing reduction in the size of glioblastoma tumors than higher doses (FIG. 11).

Figure 10:
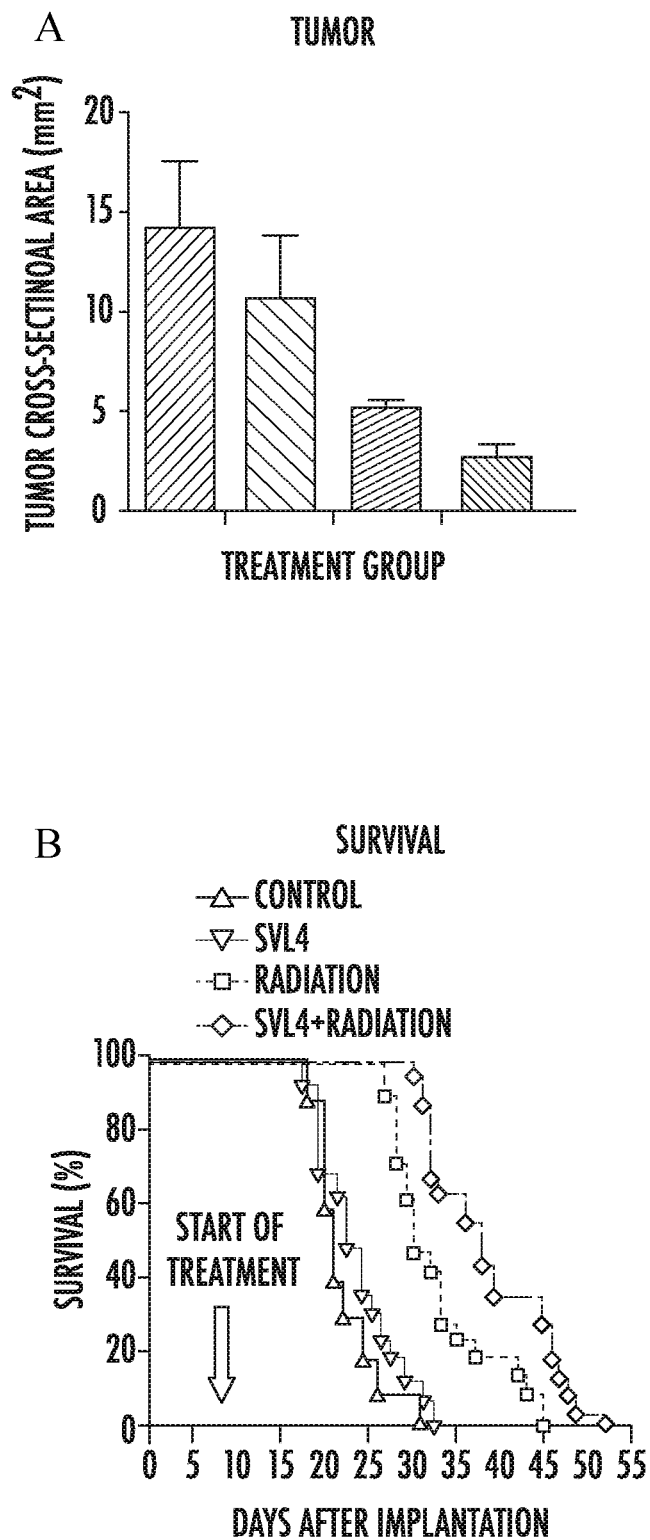
FIG. 10 depicts the tumor size at day 19 after implantation of glioma cells in the brain of mice (A) and survival of mice implanted with glioma cells in the brain (B). A low dose of radiation was given on day 7 and 9, followed by subcutaneous injection of svL4 (1 nmol/g body weight) on alternate days thereafter.

Ionizing radiation has a synergistic effect with peptide on the immune system, as shown in FIG. 10. Indeed, success in cancer treatment has been found to be largely contingent upon synergy of radiotherapy with the host's immune response. However, high-dose radiation, defined as greater than 1 Gy, is immunosuppressive. Nevertheless, radiation up-regulates stress proteins in cancer cells, which improves the ability of antigen-presenting cells to initiate an antitumor response to clear damaged cells by phagocytosis or cytolytic activity [reviewed in Manda et al., 2012].

A similar experiment was performed in which the therapeutic agent was α-PD-1 antibody. As with svL4, improved survival was demonstrated with combination α-PD-1 therapy plus radiation. Median survival was 25 days for control mice, 27 days in the α-PD-1 only group, 28 days in the radiation arm, and 53 days in the radiation plus α-PD-1 group [Zeng et al., 2013]. Viewing these experiments together, a combination therapy of svL4 with α-PD-1 plus radiation should provide long-term survival.

Immunotherapy may therefore be optimized by administration of appropriate doses of svL4 combined with other therapies such as α-PD-1, α-PD-L1 and low-dose radiation. It is expected that treatment with this combination will be synergistic and show dramatic improvement in survival of patients that are initially subjected to surgical debulking of the glioblastoma tumor.

8. Treatment of Ovarian Cancer with svL4

Figure 12:
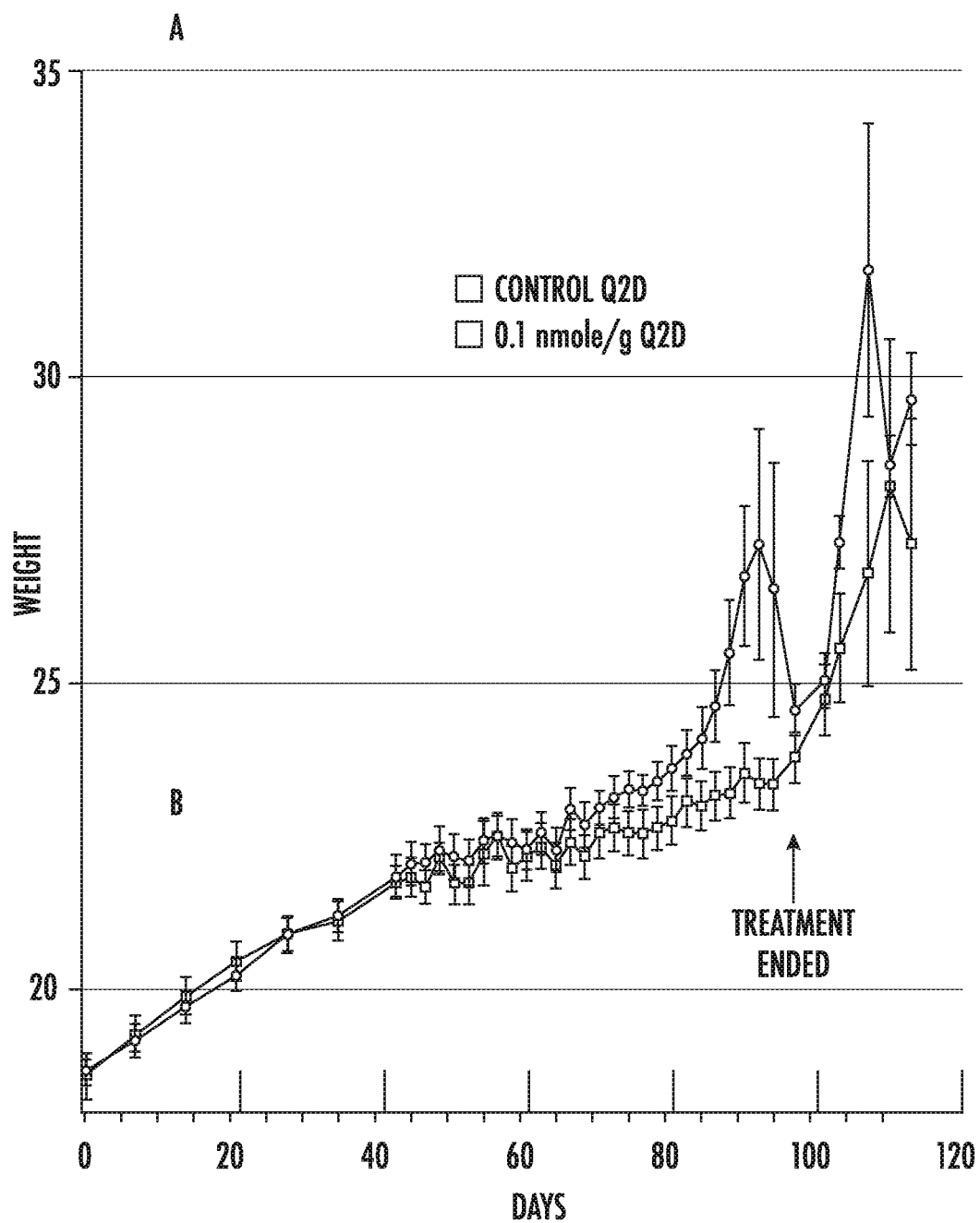
FIG. 12 depicts the effect of treatment on mice implanted with an ovarian cancer cell line. A: Average body weight of groups of 8 C57BL/6 mice treated with 0.1 nmol/g svL4 subcutaneously from day 45 to day 98 (lower line) or untreated (upper line). The rapid drops in the average body weight of control mice near day 90 indicated death of animals. Interestingly, when treatment was terminated, ascites seemed to increase. B: Survival curves of untreated and treated mice after end of treatment at day 95. Whereas all untreated animals died by day 129, four of the eight treated animals were alive at day 150 in the 0.1 nmol/g group, which is 8 weeks after the termination of treatment.
Figure 12:
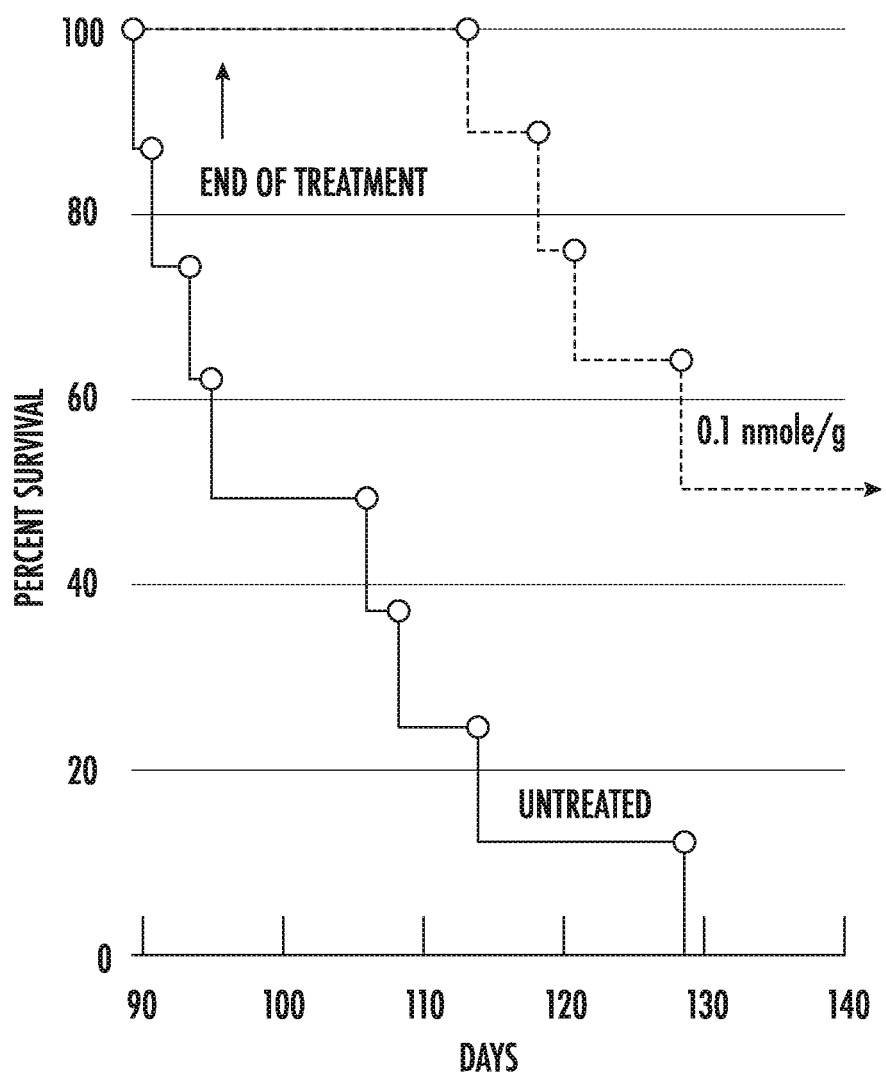

Further evidence for optimal concentrations of svL4 near 0.1 nmol/g was obtained in an experiment with a mouse model of ovarian cancer (Roby et al., 2000). An ovarian cancer cell line was implanted into the peritoneal cavity of C57BL/6 female mice, and treatment with tetravalent svL4 began 45 days later, to mimic a late stage at which most women are diagnosed. Treatment was continued for 50 days, and progression of the cancer was monitored by body weight of animals as an indication of ascites development. (Ascites is a term that describes abnormal accumulation in the abdomen of fluid that contains free-floating tumor cells.) In this system, tumor progression in the peritoneal cavity is initially slow but then progresses rapidly, with ultimate development of tumor ascites. Body weight of control animals increased rapidly starting about day 70 (FIG. 12A), and by day 129 all control mice had died (FIG. 12B). Body weight of animals treated with 0.1 nmol/g did not increase beyond the rate of normal growth and all 8 animals were alive at day 110, 20 days after the end of treatment (FIG. 12B), and 4 of 8 were still alive at day 150. One animal that was treated with 1 nmol/g died during treatment (near day 80) but only one more died up to day 130. After treatment ended, weight of animals eventually increased, which suggested that treatment with svL4 suppressed development of ascites but did not eliminate the tumors. However, five weeks after cessation of treatment, the surviving mice appeared well. It is possible that continued treatment would suppress formation of ascites indefinitely. Importantly, most of the mice continued to live for weeks after cessation of treatment, which suggested development of memory B cells A wide range of immune-modulating approaches are currently being evaluated for treatment of ovarian cancer, including a number of monoclonal antibodies such as α-CTLA-4 (ipilimumab), α-CA-125 (oregovomab) and α-PD-L1 [Tse et al., 2014]. Early results from clinical studies have been mostly disappointing because patients are usually diagnosed with late-stage disease. As shown in FIG. 12, svL4 controlled late-stage ovarian cancer, possibly indefinitely, and therefore should be an opportunistic complement to checkpoint blockage antibodies. This combination therapy should rescue immunotherapy with antibodies from the confines of use as a short-term adjunct regimen.

Comparison of all treatments, the three doses and the two frequencies of administration (Monday/Wednesday, MW, or every other day, Q2D) is shown in Table 4. The median survival comparison showed that the dose of 0.1 nmol/g, administered every other day, provided maximal extension of survival.

TABLE 4

Median survival in days and percent animals surviving at 100, 120 and 140 days post cancer cell injection.

|  | PBS Q2D | PBS MW | svL4 0.1 nmol/g Q2D | svL4 0.1 nmol/g MW | svL4 1.0 nmol/g Q2D | svL4 1.0 nmol/g MW | svL4 10 nmol/g Q2D | svL4 10 nmol/g MW |
|---|---|---|---|---|---|---|---|---|
| Median Survival (days) | 108.5 | 114.5 | 146.0 | 126.0 | 130.0 | 137.5 | 137.5 | 132.5 |
| % survival at 100 days | 62.5 | 75.0 | 100 | 100 | 87.5 | 100 | 87.5 | 87.5 |
| % survival at 120 days | 25.0 | 25.0 | 87.5 | 75.0 | 75.0 | 62.5 | 75.0 | 87.0 |
| % survival at 140 days | 0 | 0 | 50.0 | 12.5 | 12.5 | 50 | 50 | 37.5 |

It is important to note that during and after drug administration there was no change in mouse weight or behavior, indicating no overt toxicity related to treatment. Repeated injection of drug in the same region resulted in no apparent irritation or formation of fibrous or granulomatous tissue. Furthermore, attempts to detect binding of peptides to sera from mice treated for 100 days with svL4 were negative, which suggested that the peptide is not antigenic in mice.

9. Efficacy of IV Injections of svL4 into Dogs with a Variety of Cancers

Figure 13:
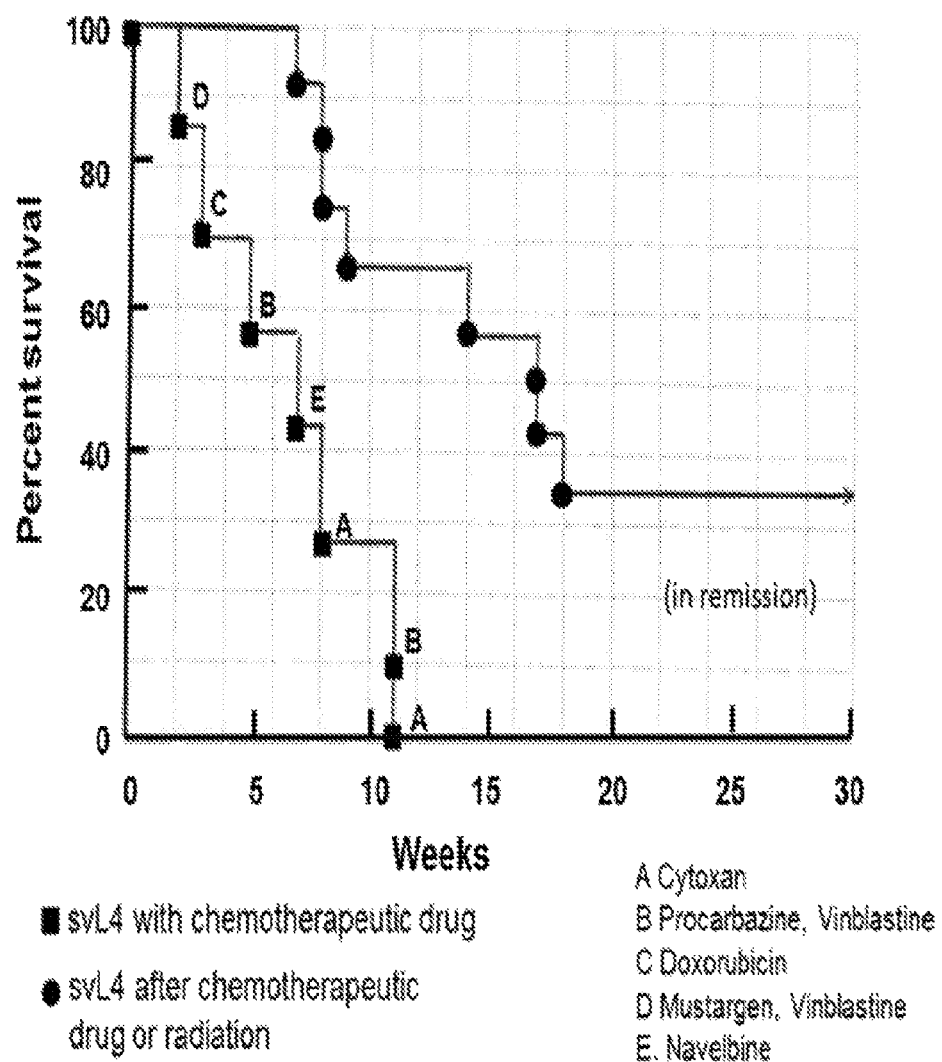
FIG. 13 depicts a comparison of the survival of dogs with a variety of cancer when treated with chemotherapeutic drugs (listed) plus svL4 or only svL4 after termination of other drugs. Injections of 1 mg were given intravenously on a weekly schedule.

In a preliminary study of the effect of low doses of svL4 in dogs with several cancers, weekly injections of tetravalent svL4 alone was effective in significantly extending life beyond that provided by standard chemotherapeutic drugs, even when combined with svL4 (FIG. 13). These data suggest that chemotherapeutic drugs interfere with the immunostimulatory action of svL4. Thus this combination immunotherapy is best used without chemotherapy. It would therefore be of advantage to provide svL4 and α-CTLA-4 or α-PD-1 as a mixture within a single injection. The doses of each component can be adjusted individually to obtain optimal benefit, for example at a frequency of weekly injections.

REFERENCES

1. Curan M A, Montalvo W, Yagita H, Allison J P. 2010. PD-1 and CTLA-4 combination blockade expands infiltrating T cells and reduces regulatory T and myeloid cells within B16 melanoma tumors. Proc Natl Acad Sci USA 107:4274-4280.
2. Degli-Esposti M A, Smyth M J. 2005. Close encounters of different kinds: dendritic cells and NK cells take centre stage. Nat Rev Immunol 5:112-124.
3. Dwyer K M, Hanidziar D, Putheti P, and 10 co-authors. 2010. Expression of CD39 by human peripheral blood CD4$^+$CD25$^+$ T cells denotes a regulatory memory phenotype. Am J Transplant 10:2410-2420.
4. Eggink L L, Hoober J K. 2009. A biologically active peptide mimetic of N-acetylgalactosamine/galactose. BMC Res Notes 2:23.
5. Eggink L L, Hoober J K. 2010. Peptide mimetics of terminal sugars of complex glycans. Glycobiol Insights 2:63-74.
6. Freeman G J, Long A J, Iwai Y, Bourque K, Chernova T, Nishimura H, Fitz L J, Malenkovich N, Okazaki T, Byrne M C, Horton H F, Fouser L, Carter L, Ling V, Bowman M R, Carreno B M, Collins M, Wood C R, Honjo T. 2000. Engagement of the PD-1 immunoinhibitory receptor by a novel B7 family member leads to negative regulation of lymphocyte activation. J. Exp. Med. 192: 1027-1034.
7. Garcia-Vallejo J J, van Kooyk Y. 2009. Endogenous ligands for C-type lectin receptors: the true regulators of immune homeostasis. Immunol Rev 230:22-37.
8. Geijtenbeek T B H, Gringhuis S I. 2009. Signalling through C-type lectin receptors: shaping immune responses. Nature Rev Immunol 9:465-479.
9. Hanahan D, Weinberg, R A. 2011. Hallmarks of Cancer: The Next Generation. Cell 144:646-674.
10. Ishida Y, Agata Y, Shibahara K, Honjo T. 1992. Induced expression of PD-1, a novel member of the immunoglobulin gene superfamily, upon programmed cell death. EMBO J. 11: 3887-3895.
11. Iwai Y, Ishida M, Tanaka Y, Okazaki T, Honjo T, Minato N. 2002. Involvement of PD-L1 on tumor cells in the escape from host immune system and tumor immunotherapy by PD-L1 blockade. Proc. Natl. Acad. Sci. U.S.A. 99:12293-12297.
12. Joannes F M, Idema A J, Bol K F, and 7 co-authors. 2009. Regulatory T cells and the PD-L1/PD-1 pathway mediate immune suppression in malignant brain tumors. Neuro-Oncology 11:394-402.
13. Kushchayev S V, Sankar T, Eggink, L L, Kushchayeva Y S, Wiener P C, Hoober J K, Eschbacher J, Liu R, Shi F-D, Abdelwahab M, Scheck A C, Preul M C. 2012. Monocyte galactose/N-acetylgalactosamine specific C-type lectin receptor stimulant immunotherapy of an experimental glioma. Part 1: stimulatory effects on blood monocytes and monocyte-derived cells of the brain. Cancer Manag Res 20:309-323.
14. Kushchayev S V, Sankar T, Eggink L L, Kushchayeva Y S, Wiener P C, Hoober J K, Eschbacher J, Liu R, Shi F-D, Abdelwahab M, Scheck A C, Preul M C. 2012. Monocyte galactose/N-acetylgalactosamine-specific C-type lectin receptor stimulant immunotherapy of an experimental glioma. Part II: combination with external radiation improves survival. Cancer Manag Res 20:325-334.
15. Latchman Y, Wood C R, Chernova T, Chaudhary D, Borde M, Chernova I, Iwai Y, Long A J, Brown J A, Nunes R, Greenfield E A, Bourque K, Boussiotis V A, Carter L L, Carreno B M, Malenkovich N, Nishimura H, Okazaki T, Honjo T, Sharpe A H, Freeman G J. 2001. PD-L2 is a second ligand for PD-1 and inhibits T cell activation. Nat. Immunol. 2: 261-268.
16. McNeill L, Salmond R J, Cooper J C, and 6 co-authors. 2007. The differential regulation of Lck kinase phosphorylation sites by CD45 is critical for T cell receptor signaling responses. Immunity 27:425-437.
17. Manda K, Glasow A, Paape D, Hildebrandt G. 2012. Effects of ionizing radiation on the immune system with special emphasis on the interaction of dendritic cells and T cells. Frontiers Oncol 2:article 102.
18. Quezada S A, Peggs K S, Curran M A, Allison J P. 2006. CTLA4 blockade and GM-CSF combination immunotherapy alters the intratumor balance of effector and regulatory T cells. J Clin Invest 116:1935-1945.
19. Roby K F, Taylor C C, Sweetwood J P, Cheng Y, Pace J L, Tawfik O, Persons D L, Smith P G, Terranova P F.

2000. Development of a syngeneic mouse model for events related to ovarian cancer. Carcinogenesis 21:585-591.

20. Roskoski R Jr. 2005. Src kinase regulation by phosphorylation and dephosphorylation. Biochem Biophys Res Commun 331:1-14.
21. Sim G C, Martin-Orozco N, Jin L, and 8 co-authors. 2014. IL-2 therapy promotes suppressive ICOS+ Treg expansion in melanoma patients. J Clin Invest 124:99-110.
22. Simpson T R, Li F, Montalvo-Ortiz, 11 additional co-authors. 2013. Fc-dependent depletion of tumor-infiltrating regulatory T cells co-defines the efficacy of anti-CTLA-4 therapy against melanoma. J Exp Med 210: 1695-1710.
23. Sonnenschein C, Soto A M, Rangarajan A, Kulkarni P. 2014. Competing views on cancer. J Biosci 39:281-302.
24. Streng-Ouwehand I, Unger W W J, van Kooyk Y. 2011. C-type lectin receptors for tumor eradication: future directions. Cancers 3:3169-3188.
25. Teicher B A. 2006. Tumor models for efficacy determination. Mol Cancer Ther 5:2435-2443.
26. Topalian S L, Sznol M, McDermott D F, and 18 co-authors. 2014. Survival, durable tumor remission, and long-term safety in patients with advanced melanoma receiving Nivolumab. J Clin Oncol 32:1020-1030.
27. Trowbridge I S, Thomas M L. 1994. CD45: an emerging role as a protein tyrosine phosphatase required for lymphocyte activation and development. Annu Rev Immunol 12:85-116.
28. Tse B W G, Collins A, Oehler M K, Zippelius A, Heinzelmann-Schwaarz V A. 2014. Antibody-based immunotherapy for ovarian cancer: where are we at? Ann Oncol 25:322-331.
29. van Vliet S J, Gringhuis S I, Geijtenbeek T B H, van Kooyk Y. 2006. Regulation of effector T cells by antigen-presenting cells via interaction of the C-type lectin MGL with CD45. Nature Immunol 7:1200-1208.
30. van Vliet S J, Saeland E, van Kooyk Y. 2008. Sweet preferences of MGL: carbohydrate specificity and function. Trends Immunol 29:83-90.
31. Weber, J. 2010. Immune checkpoint proteins: a new therapeutic paradigm for cancer—preclinical background: CTLA-4 and PD-1 blockade. Semin. Oncol. 37 (5): 430-439.
32. Wolchok J D, Kluger H, Callahan M K, and 21 co-authors. 2013. Nivolumab plus ipilimumab in advanced melanoma. N Engl J Med 369:122-33.
33. Zhao J, Zhao J, Perlman S. 2012. Differential effects of IL-12 on Tregs and non-Treg T cells: roles of IFN-c, IL-2 and IL-2R. PLoS ONE 7:e46241.
34. Zeng J, See A P, Phallen J, and 18 co-authors. 2013. Anti-PD-1 blockade and stereotactic radiation produces long-term survival in mice with intracranial gliomas. Int J Rad Oncol Biol Phys 86:343-349.

What is claimed is:

1. A pharmaceutical composition comprising a therapeutically effective amount of a peptide and a therapeutically effective amount of a first antibody,
   wherein the peptide comprises the active sequence represented by SEQ ID NO:1, and
   the first antibody is a fully human, monoclonal antibody against CTLA-4, ipilimumab.

2. The pharmaceutical composition of claim 1, further comprising a pharmaceutically acceptable carrier.

3. The pharmaceutical composition of claim 1, wherein the combination is sufficient to increase the population of effector T cells ($CD3^+$, $CD4^+$, $CD25^-$, $CD39^-$).

4. The pharmaceutical composition of claim 1, wherein the combination is sufficient to reduce the population of regulatory T cells within tumors, and to increase the levels of at least one anti-cancer cytokines selected from the group consisting of: IL-2, IL-12p70, IL-21, IL-27, TNFα, and IFNγ in a subject having cancer.

5. The pharmaceutical composition of claim 4, wherein cancer is selected from the group consisting of: bladder cancer, brain cancer, breast cancer, colon cancer, head and neck cancer, liver cancer, lung cancer, pancreatic cancer, prostate cancer, ovarian cancer, kidney cancer, and skin cancer.

6. The pharmaceutical composition of claim 5, wherein cancer is selected from the group consisting of: colorectal adenocarcinoma, glioblastoma, hepatocellular carcinoma, hormone-refractory prostate cancer, epithelial ovarian carcinoma, ovarian adenocarcinoma, melanoma, mesothelioma, non-small cell lung cancer, small cell lung cancer, and renal cell carcinoma.

7. A method of increasing the population of effector T cells ($CD3^+$, $CD4^+$, $CD25^-$, $CD39^-$) in a subject, the method comprising:
   administering a therapeutically effective amount of the pharmaceutical composition of claim 1 to the subject.

8. The method of claim 7, wherein the subject has cancer, and the method further comprising administering radiation treatment to the subject.

9. A kit comprising:
   a therapeutically effective amount of a peptide, wherein the peptide comprises the active sequence represented by SEQ ID NO:1; and
   a therapeutically effective amount of a fully human, monoclonal antibody against CTLA-4, ipilimumab.

10. The method of claim 7, wherein the therapeutically effective amount of the peptide is between about 0.1 nmol/kg body weight to about 1500 nmol/kg body weight.

11. The method of claim 10, wherein the therapeutically effective amount of the peptide is between about 1 nmol/kg body weight to about 1000 nmol/kg body weight.

12. The method of claim 10, wherein the therapeutically effective amount of the peptide is about 1 nmol/kg body weight.

13. The pharmaceutical composition of claim 1, wherein the peptide is tetravalent.

14. The pharmaceutical composition of claim 13, wherein the active sequence is connected to a tri-lysine core by a linker sequence comprising SEQ ID NO: 2.

15. The kit of claim 9, wherein the peptide is tetravalent.

16. The kit of claim 15, wherein the active sequence is connected to a tri-lysine core by a linker sequence comprising SEQ ID NO: 2.

\* \* \* \* \*

```
                         SEQUENCE LISTING

<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 1

Val Gln Ala Thr Gln Ser Asn Gln His Thr Pro Arg
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 2

Gly Gly Gly Ser
1

<210> SEQ ID NO 3
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 3

Val Gln Ala Thr Gln Ser Asn Gln His Thr Pro Arg Gly Gly Gly Ser
1               5                   10                  15

Gly Gly Gly Ser Lys Lys Lys Lys
            20
```